(12) United States Patent
De Filette et al.

(10) Patent No.: US 7,449,188 B2
(45) Date of Patent: Nov. 11, 2008

(54) RECOMBINANT OLIGOMETRIC PROTEIN COMPLEXES WITH ENHANCED IMMUNOGENIC POTENTIAL

(75) Inventors: Marina De Filette, Brussels (BE); Tom Maria Deroo, Ghent (BE); Walter Fiers, Destelbergen (BE); Marleen Maras, Sint-Martens-Lierde (BE); Willy Alfons Min Jou, Destelbergen (BE)

(73) Assignee: Vlaams Interuniversitair Instituut Voor Biotechnologie, Zwijnaarde (BE)

(*) Notice: Subject to any disclaimer, the term of this patent is extended or adjusted under 35 U.S.C. 154(b) by 75 days.

(21) Appl. No.: 10/466,655

(22) PCT Filed: Jan. 18, 2002

(86) PCT No.: PCT/EP02/00628

§ 371 (c)(1),
(2), (4) Date: Jul. 18, 2003

(87) PCT Pub. No.: WO02/074795

PCT Pub. Date: Sep. 26, 2002

(65) Prior Publication Data

US 2004/0116664 A1 Jun. 17, 2004

(30) Foreign Application Priority Data

Jan. 18, 2001 (EP) .................................. 01200193

(51) Int. Cl.
| | |
|---|---|
| A61K 39/145 | (2006.01) |
| A61K 39/385 | (2006.01) |
| C07K 19/00 | (2006.01) |
| C07K 14/11 | (2006.01) |
| C12N 15/62 | (2006.01) |
| C12N 15/44 | (2006.01) |
| C12N 15/63 | (2006.01) |
| C12N 1/21 | (2006.01) |
| C12N 5/10 | (2006.01) |

(52) U.S. Cl. ............................... 424/192.1; 424/196.11; 424/209.1; 424/210.1; 530/350; 536/23.4; 536/23.72; 435/320.1; 435/325; 435/252.3

(58) Field of Classification Search .............. 424/210.1, 424/206.1, 192.1, 196.11, 204.1, 1.49, 135.1, 424/159.1; 530/350, 387.3; 435/69.1, 69.7, 435/5; 536/23.4
See application file for complete search history.

(56) References Cited

U.S. PATENT DOCUMENTS

| 5,463,024 | A | | 10/1995 | Kingsman et al. ........... 530/350 |
| 5,721,340 | A | * | 2/1998 | Halazonetis ................ 530/350 |
| 7,229,624 | B2 | * | 6/2007 | Renner et al. .......... 424/196.11 |

FOREIGN PATENT DOCUMENTS

| WO | WO 94/10308 | | 5/1994 |
| WO | WO 99/62953 | * | 12/1999 |
| WO | WO 00/32227 | | 6/2000 |
| WO | WO 0069907 A1 | * | 11/2000 |
| WO | WO 01/02440 | | 1/2001 |
| WO | WO 01/49886 | | 7/2001 |
| WO | WO 01/49886 A2 | | 7/2001 |
| WO | WO 01/59886 A3 | | 7/2001 |

OTHER PUBLICATIONS

Chang, C. et al., Phenotype mixing between different hepadnavirus nucleocapsid proteins revels C protein dimerization to be cis preferential. J. Virol. Aug. 1994;68(8):5225-31.*

Fields Virology, 3rd Ed. edited by Fields, B.N. et al. Lippincott—Raven Publishers, Philadelphia, 1996, "Orthomyxoviridae:The Viruses and their Replication" pp. 1355 and 1362-1365.*

Weissenhorn, W. et al. Assembly of a rod-shaped chimera of a trimeric GCN4 zipper and the HIV-1 gp41 ectodormain expressed in *Escherichia coli*. Proc Natl Acad Sci U S A. Jun. 10, 1997;94(12):6065-9.*

Cooper et al., "Mapping of Conformational B Cell Epitopes within Alpha-Helical Coiled Coil Proteins," Molecular Immunology, vol. 34, No. 6 (433-440)(1997).*

Harbury et al., "A Switch Between Two-, Three-, and Four-Stranded Coiled Coils in GCN4 Leucine Zipper Mutants," Science, vol. 262, pp. 1401-1407 (1993).*

Landschulz et al., "The Leucine Zipper: A Hypothetical Structure Common to a New Class of DNA Binding Proteins," Science, vol. 240 pp. 1759-1763 (1988).*

Bucher, D.J., et al., "$A_2$ (N2) Neuraminidase of the X-7 Influenza Virus Recombinant: Determination of Molecular Size and Subunit Composition of the Active Unit," *J Virol*, 10:60-66 (1972).

Burton, D.R., "A Vaccine for HIV Type 1: The Antibody Perspective," *Proc. Natl. Acad. Sci. USA*, 94:10018-10023 (1997).

Chang, Z., et al., "*Mycobacterium Tuberculosis* 16-kDa Antigen (Hsp16.3) Functions as an Oligomeric Structure in Vitro to Supress Thermal Aggregation," *J Biol Chem*, 271:7218-7223 (1996).

Bowie, J.U., et al., "A Method to Identify Protein Sequences that Fold into a Known Three-Dimensional Structure," *Science*, 253:164-170 (1991).

Deroo, T., et al., "Recombinant Neuraminidase Vaccine Protects Against Lethal Influenza," *Vaccine*, 14:561-569 (1996).

Kodihalli, S., et al., "Selection of a Single Amino Acid Substitution in the Hemagglutinin Molecule by Chicken Eggs Can Render Influenza A Virus (H3) Candidate Vaccine Ineffective," *J Virol*, 69:4888-4897 (1995).

(Continued)

*Primary Examiner*—Mary E Mosher
(74) *Attorney, Agent, or Firm*—Husch Blackwell Sanders Welsh and Katz

(57) ABSTRACT

The present invention relates to a chimeric protein comprising an antigen and an oligomerisation domain. The present invention relates further to recombinant oligomeric protein complexes comprising said chimeric protein and the use thereof for the manufacture of a vaccine.

11 Claims, 14 Drawing Sheets

OTHER PUBLICATIONS

Lin, X.H., et al., "Deletion of the Carboxy-Terminus of Herpes Simplex Virus Type 1 (HSV-1) Glycoprotein B Does Not Affect Oligomerization, Heparin-Binding Activity, or its Ability to Protect Against HSV Challenge," *Arch Virol*, 141:1153-1165 (1996).

Neirynck, S., et al., "A Universal Influenza A Vaccine Based on the Extracellular Domain of the M2 Protein," *Nature Medicine*, 5:1157-1163 (1999).

Sanchez, J., et al., "Recombinant Cholera Toxin B Subunit and Gene Fusion Proteins for Oral Vaccination," *Res. Microbiol.*, 141:971-979 (1990).

Sugrue, R.J., et al., "Structural Characteristics of the M2 Protein of Influenza A Viruses: Evidence that It Forms A Tetrameric Channel," *Virology*, 180:617-624 (1991).

Varghese, J.N., et al., "Structure of the Influenza Virus Glycoprotein Antigen Neuraminidase at 2.9 A Resolution" *Nature*, 303:35-40 (1983).

Ward, C.W., et al., "The Disulphide Bonds of an Asian Influenza Virus Neuraminidase," *FEBS Lett*, 153:29-33 (1983).

Winkler, G., et al., "Evidence that the Mature Form of the Flavivirus Nonstructural Protein NS1 is a Dimer," *Virology*, 162:187-196 (1988).

* cited by examiner

Fig. 10

118 kDa
81 kDa
52.5 kDa
36.2 kDa
29.9 kDa
20.7 kDa 7.1 kDa — ← sM2eGCN4

A  Detection of antibodies of isotype IgG1 directed against M2e peptide in serum of immunized mice B  Detection of antibodies of isotype IgG1 directed against M2eGCN4C3d in serum of immunized mice (precoating with anti-C3)

RECOMBINANT OLIGOMETRIC PROTEIN COMPLEXES WITH ENHANCED IMMUNOGENIC POTENTIAL

The present invention relates to a chimeric protein comprising an antigen and an oligomerisation domain. The present invention relates further to recombinant oligomeric protein complexes comprising said chimeric protein and the use thereof for the manufacture of a vaccine. Many of the natural occurring antigens, irrespective of their origin, are oligomeric in nature. Some non-limiting examples are Hsp16.3 of *Mycobacterium tuberculosis* and several bacterial toxins. Hsp16.3, an immunodominant antigen of *Mycobacterium tuberculosis* with serodiagnostic value, occurs as an oligomeric structure, presumably based on trimers (Chang et al, 1996). Cholera toxin as well as the closely related heat-labile toxin from *Escherichia coli* is composed of two subunits, A and B, which form an oligomeric assembly $AB_5$. The B subunit portion of cholera toxin can be used as an immunizing agent in humans, providing protection against both cholera and diarrhoea caused by enterotoxigenic *E. coli* (Sanchez et al. 1990). In a similar way, B oligomer, which is a constituent of pertussis toxin, can be used to elicit immunoprotective responses against *Bordetella pertussis*.

Also viral antigens occur often as oligomeric structures. As non-limiting examples, we can cite the herpes simplex virus type 1 glycoprotein B (Lin et al., 1996) or the flavivirus non-structural protein NS1, which has been used in a recombinant vaccine against dengue-2 and which exists normally as a homodimer in infected cells (Winkler et al., 1988). The HIV-1 envelope molecules gp41 and gp120, which may be interesting targets for vaccine development, likewise form an oligomeric structure (Burton, 1997). The predominant antigens of influenza virus are also oligomers. Haemagglutinin (HA) occurs naturally as a homotrimer. Neuraminidase (NA) occurs naturally as a homotetramer, composed of two disulphide-linked dimers, which are held together by non-covalent interactions (Laver and Valentine, 1969; Bucher and Kilbourne, 1972; Varghese et al., 1983; Ward et al., 1983). Influenza M2-protein also occurs normally as a homotetramer.

Most of the vaccines on the market are either inactivated or attenuated life vaccines. These vaccines are often produced in animal cell culture, implying a high level of biohazard because of the direct handling of pathogenic viruses, and with a high production cost due to expensive raw materials and complicated product processes.

Although the oligomeric antigens are presumed to keep their oligomeric structure in these vaccines, this is not always the case. For example in the preparation of influenza split vaccines, the oligomeric antigens may lose their oligomeric structure during the viral disruption step. For influenza viruses, there is an additional complication due to the fact that they undergo significant antigenic variation in their two surface antigens haemagglutinin (HA) and neuraminidase (NA) (antigenic drift). Due to the variability of these two proteins a broad spectrum, long lasting vaccine against influenza has so far not been developed. The influenza vaccine commonly used has to be adapted almost every year to follow the antigenic drift. When more drastic changes occur in the virus, known as antigenic shift, a previous vaccine is no longer protective. The present vaccines are based on virus material that has been produced in chicken eggs. Although these vaccine preparations have been found to be effective against an influenza infection caused by the homologous virus strain, there are several drawbacks, such as the production time, which makes it impossible to put an adapted vaccine on the market on short term notice. Moreover, considering the antigenic drift or even the sudden appearance of a shift variant, there is the added risk of selecting antigenic variants of the virus by the growth process in the eggs itself (Koduhalli et al., 1995).

Therefore, considerable effort has been put in the development of recombinant vaccines. Recombinant vaccines can be based on selected epitopes and are generally safer and cheaper to produce. Moreover, as described e.g. in WO9319185, in recombinant vaccines, the antigen can be fused to immunostimulatory domains to avoid or limit the use of adjuvant in the vaccine preparation, or to boost the immune response of weakly immunogenic epitopes. Recombinant vaccines have been developed against several major diseases, such as measles, tetanus, pertussis, TBC, hepatitis B, cholera and influenza. Several others, such as e.g. a recombinant vaccine against HIV, are under development.

As an example, recombinant vaccines against influenza virus have been described in WO9406468, WO9407533, WO9518861 and WO9520660. Moreover, a recombinant vaccine based on the membrane protein M2 has been developed, which has the additional advantage to induce a broad spectrum, long-term protection (Neirynck et al., 1999; WO9303173, WO9907839, WO9928478).

Both NA (Laver and Valentine, 1969; Bucher and Kilbourne, 1972; Varghese et al., 1983; Ward et al., 1983) and M2 (Sugrue and Hay, 1991) occur naturally as homotetramers. However, recombinant preparations of NA only partly yield homotetramers, the major part of the preparation being monomers and dimers.

Although one might expect that antigenic epitopes are as well, if not better accessible in these mono- and dimers, surprisingly, we found that tetrameric molecules were considerably superior in eliciting a specific antibody response. Although tetrameric preparations of these molecules can be obtained by an additional purification step of the recombinant protein, such as size exclusion chromatography, such purification would lead to an important loss in yield. Furthermore, renewed dissociation of the purified material cannot be excluded. By fusing an oligomerisation domain to the influenza antigen, a spontaneous tetramerisation could be obtained of the fusion protein, yielding a recombinant protein in an almost purely tetrameric form. Surprisingly, we found that these fusion tetramers showed a similar enhanced antigenic capacity as the purified tetrameric, recombinant protein.

It is the object of the invention to provide a highly immunogenic recombinant antigen protein complex, preferably a recombinant influenza antigen protein complex.

It is a first aspect of the invention to provide a chimeric protein comprising antigen, derived from a naturally occurring oligomeric protein complex, and an oligomerisation domain. Said oligomerisation domain is heterologous, i.e. it is derived from another protein than the antigen. The oligomerisation domain is driving the oligomerisation of the chimeric protein to form a recombinant oligomeric protein complex. Preferentially, the degree of oligomerisation (dimeric, trimeric, tetrameric or higher) of the chimeric protein is identical to the degree of oligomerisation of the naturally occurring protein complex from which the antigen is derived and the antigenic domain of the chimeric protein is presented in a tertiary structure that is similar or identical to that of the tertiary structure of the antigenic domain in the naturally occurring protein. Preferably, said antigen is an influenza antigen. More preferably, said antigen is influenza neuraminidase or influenza M2-protein or a functional fragment thereof. Most preferably, said antigen is chosen from the group consisting of influenza A neuraminidase, influenza A M2 or influenza B NB-protein. Oligomerisation domains are known to the people skilled in the art and have, amongst others, been described in WO9637621, WO9818943, WO9856906, WO9962953 and WO0069907. Preferentially, the oligomerisation domain is a leucine zipper. More preferentially, the oligomerisation domain is a leucine zipper derived from the yeast transcription factor GCN4, or a modified form thereof. Most preferentially, the oligomerisation domain is a modified leucine zipper, derived from the yeast transcription factor GCN4, as described by Harbury et al. (1993). A preferred embodiment of the invention is the influenza B neuraminidase or a functional fragment thereof such as the neuraminidase B ecto-domain, fused to an oligomerisation domain such as a modified leucine zipper, derived from the yeast transcription factor GCN4, as described by Harbury et al. (1993). Another preferred embodiment is the influenza B NB-protein, or a functional fragment thereof, fused to an oligomerisation domain.

It is an aim of the present invention to present the recombinant protein complex in a conformation that resembles the conformation of the naturally occurring protein complex. In cases where the naturally occurring protein complex has a defined enzymatic activity, as is the case for influenza neuraminidase, the recombinant protein complex will have a comparable enzymatic activity.

Apart for the oligomerisation domain and the antigen, the chimeric protein may comprise other polypeptide sequences, such as linker sequences or polypeptide sequences that enhance the immune response. Such polypeptide sequences that enhance the immune response are known to the person, skilled in the art and include, as a non-limiting example, one or more copies of the third complement protein fragment d (C3d; Dempsey et al., 1996) or tetanus toxin fragment C, or *Escherichia coli* enterotoxin fragment A or B, or T-cell epitopes derived from the same pathogen as the antigen.

Another aspect of the invention is a recombinant oligomeric protein complex comprising a chimeric protein according to the invention. Preferentially, said recombinant oligomeric protein complex is a dimer, or a tetramer. More preferentially, said recombinant oligomeric protein complex is a homodimer or a homotetramer. Preferably, said oligomeric protein complex elicits a higher immune response than the monomeric subunit. A preferred embodiment of the invention is a recombinant oligomeric protein complex that has a comparable enzymatic activity as the naturally occurring oligomeric protein complex of which the antigen, comprised in the chimeric protein that forms said recombinant oligomeric protein complex, is derived.

Still another aspect of the invention is a nucleic acid, encoding a chimeric protein according to the invention. A preferred embodiment is a nucleic acid, comprising the sequence presented in SEQ ID N° 1. Another preferred embodiment is a nucleic acid, comprising the sequence presented in SEQ ID N° 3. Still another preferred embodiment is a nucleic acid comprising the sequence presented in SEQ ID N° 5.

A special embodiment is a nucleic acid, according to the invention that may be used in DNA vaccination. Vectors for DNA vaccination are known to the person skilled in the art and are described, amongst others, in WO9604394, WO9728259 and WO9908713. Methods for DNA vaccination have been described amongst others in WO0012121.

A further aspect of the invention is an expression vector comprising a nucleic acid according to the invention and allowing the expression of a chimeric protein, according to the invention. Said expression vector can be any eukaryotic or prokaryotic expression vector, as known to the person skilled in the art. In one preferred embodiment, the expression vector is pACGCN4NAs (Deposition at BCCM—(deposit nr LMBP 4270)), comprising the antigenic head domain of NA wherein the N-terminal part has been replaced by a modified leucine zipper derived from the yeast transcription factor GCN4, which is imposing tetramerisation (Harbury et al., 1993). This construct is fused to the secretion signal of influenza haemagglutinin and the construct is placed under control of the baculovirus polyhedrin promoter. Another preferred embodiment is pACsM2eGCN4 (deposit nr LMBP 4271), comprising the ectodomain of M2, fused at its N-terminus to the GP67 secretion signal of Baculovirus and at its C-terminus to the tetramerising, modified leucine zipper derived from the yeast transcription factor GCN4 (Harbury et al., 1993). Still another preferred embodiment is pACsM2eGCN4C3d (Deposition at BCCM—(deposit nr LMBP 4463)), where said ectodomain of M2, placed after the GP67 secretion signal of Baculovirus and fused to the GCN4 leucine zipper, is fused to the C3d domain.

Still another aspect of the invention is a host cell, transformed with an expression vector according to the invention. Said cell can be any prokaryotic or eukaryotic host cell. Transformation procedures are known to the person skilled in the art.

A further aspect of the invention is the use of a chimeric protein according to the invention and/or the use of a recombinant oligomeric protein complex according to the invention for the preparation of a vaccine against influenza. A special embodiment is the use of said chimeric protein whereby said chimeric protein comprises SEQ ID N° 2, SEQ ID N° 4 or SEQ ID N° 6. The chimeric protein may also be used to elicit monoclonal or polyclonal antibodies, using techniques known to the person skilled in the art, whereby said antibodies can be used for diagnostic or therapeutic purposes. Human or humanised antibodies may be especially useful as therapeutics for people with a decreased immune response, such as HIV patients.

Still another aspect of the invention is a vaccine against influenza, comprising a chimeric protein and/or a recombinant oligomeric protein complex according to the invention.

Still another aspect of the invention is a vaccine against influenza, comprising a substantially pure tetrameric form of a recombinant influenza antigen. In one preferred embodiment, said recombinant influenza antigen is recombinant influenza neuraminidase, or a functional fragment thereof. In another preferred embodiment, said recombinant influenza antigen is recombinant M2, or a functional fragment thereof.

More preferably, said influenza vaccine is fused to a heterologous oligomerisation domain, most preferably, said influenza vaccine is fused to the tetramerising, modified leucine zipper derived from the yeast transcription factor GCN4 (Harbury et al., 1993). A preferred embodiment is a vaccine, comprising a substantially pure tetrameric form of neuraminidase or a functional fragment thereof, whereby said substantially pure tetrameric form has an enzymatic activity that is comparable to naturally occurring influenza neuraminidase.

Still another aspect of the invention is the use of chimeric protein according to the invention and/or the use of a recombinant oligomeric protein complex according to the invention to screen inhibitors of the biological activity of the naturally occurring protein complex. A preferred embodiment is said use to screen inhibitors of influenza A or influenza B neuraminidase, or inhibitors of influenza A M2 or influenza B NB-protein.

DEFINITIONS

Chimeric protein as used here means that the protein is composed of at least two polypeptides, which do not occur in the same protein in the natural form.

Antigen as used here means an antigen, derived from a naturally occurring oligomeric protein from a pathogenic organism or micro-organism, including viruses, and can be used in a host, preferably, but not limited to a human host, to elicit an immune response against said pathogenic organism or micro-organism.

Recombinant oligomeric protein complex is a protein complex wherein at least one of the subunits is a chimeric protein comprising an oligomerisation domain.

Recombinant antigen as used here means that said antigen is produced by recombinant DNA techniques. The antigen may be produced in any prokaryotic or eukaryotic host cell, such as, as a non-limiting example, *Escherichia coli, Bacillus subtilis*, yeast such as *Saccharomyces cerevisiae* or *Kluyveromyces* sp., fungal cells, insect cells, plant cells or mammalian cells.

Comparable enzymatic activity means that both the naturally occurring protein complex and the recombinant oligomeric protein complex can perform at least one identical biochemical transformation of at least one substrate, but that the specific activity of the enzymatic complexes may differ. Identical biochemical transformation means that the substrate by the action of the enzymatic activity is transformed in an identical end product or identical end products.

Substantially pure tetrameric form of a recombinant antigen means that said recombinant antigen is at least for 80%, preferably at least for 90% in the tetrameric form.

Functional fragment of influenza neuraminidase or of influenza M2 is any fragment that can elicit an immune response against influenza virus. As a non-limiting example, a functional fragment of influenza M2 is the M2 ecto-domain.

Unless it is explicitly mentioned as DNA vaccine, vaccine as used here can be any protein based vaccine, including injectable as well as mucosal vaccines.

The sequence shown is SEQ ID NO:5, in reverse orientation.

Figure 4:
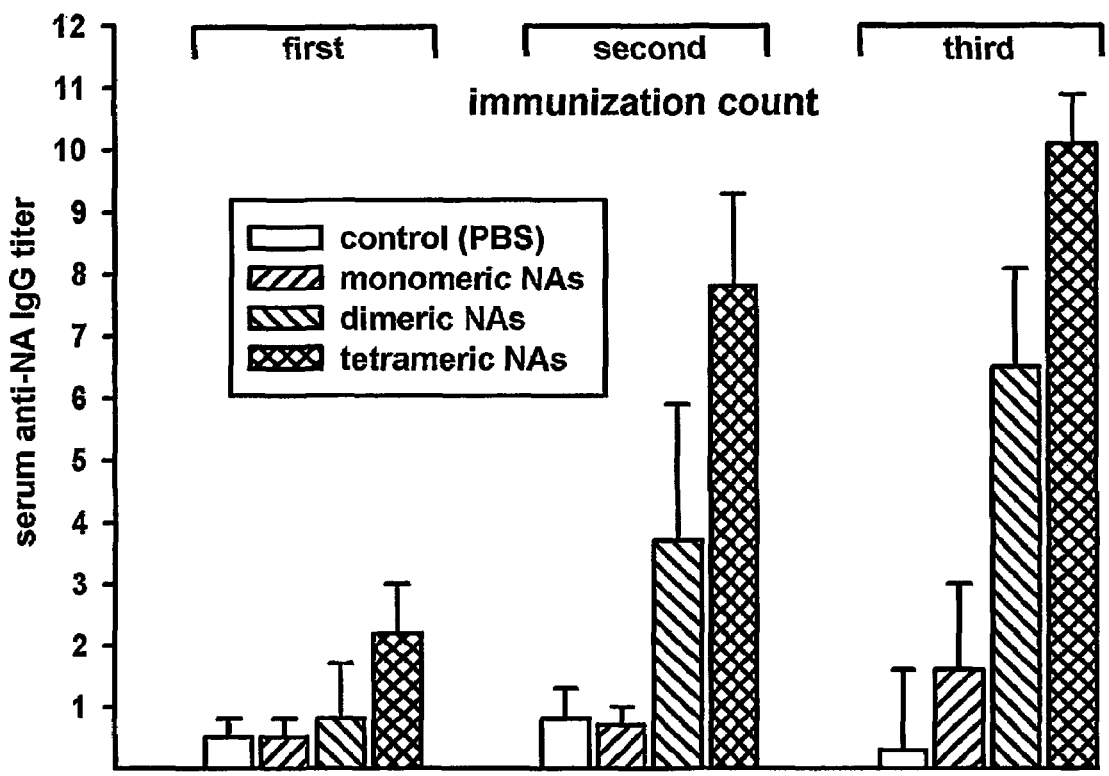

FIG. 4: Antibody response against different oligomeric subforms of recombinant neuraminidase.

Figure 5:
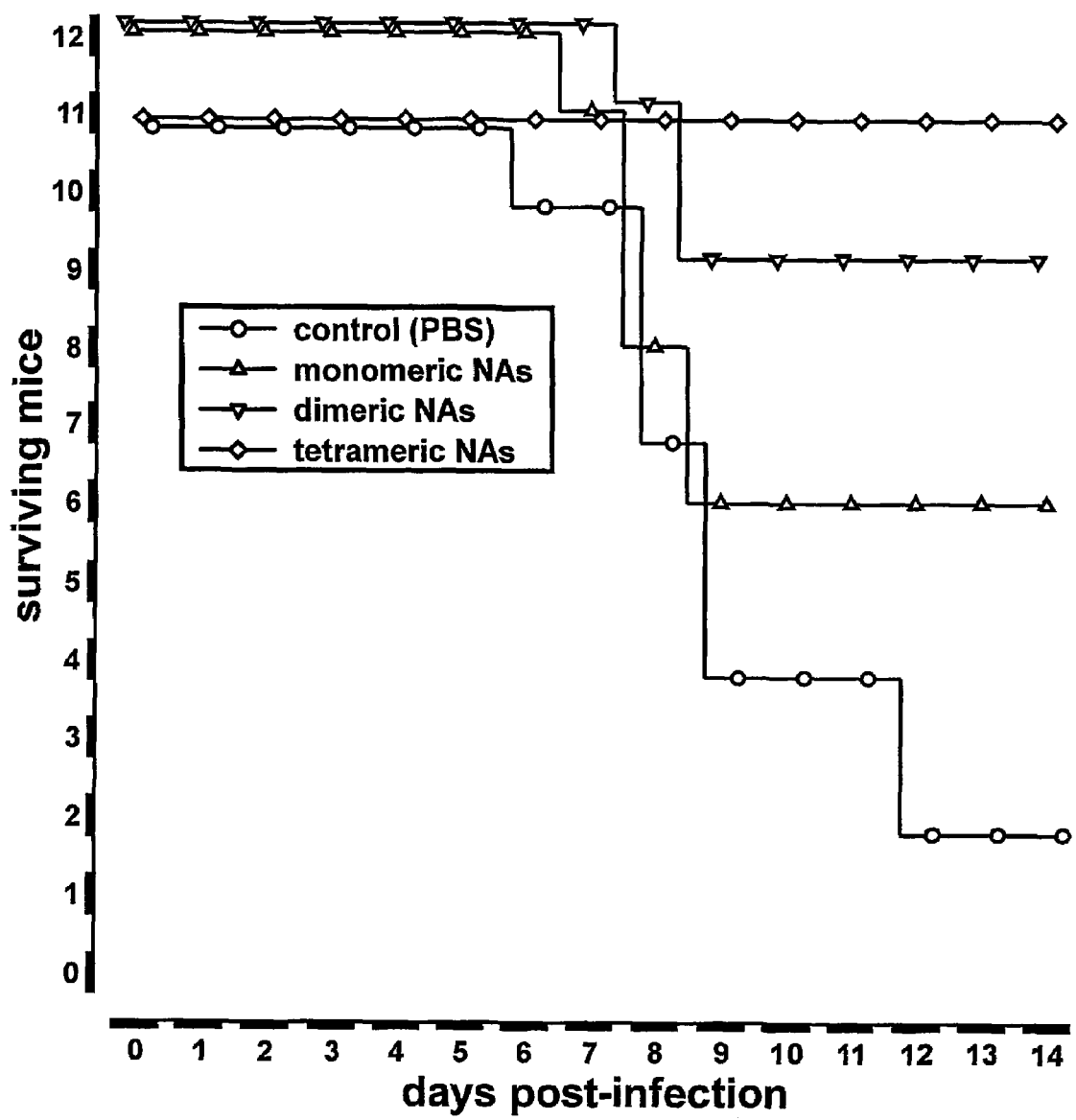

FIG. 5: Survival of mice vaccinated with different oligomeric subforms of recombinant neuraminidase after a lethal challenge with homologous, mouse-adapted influenza virus.

Figure 6:
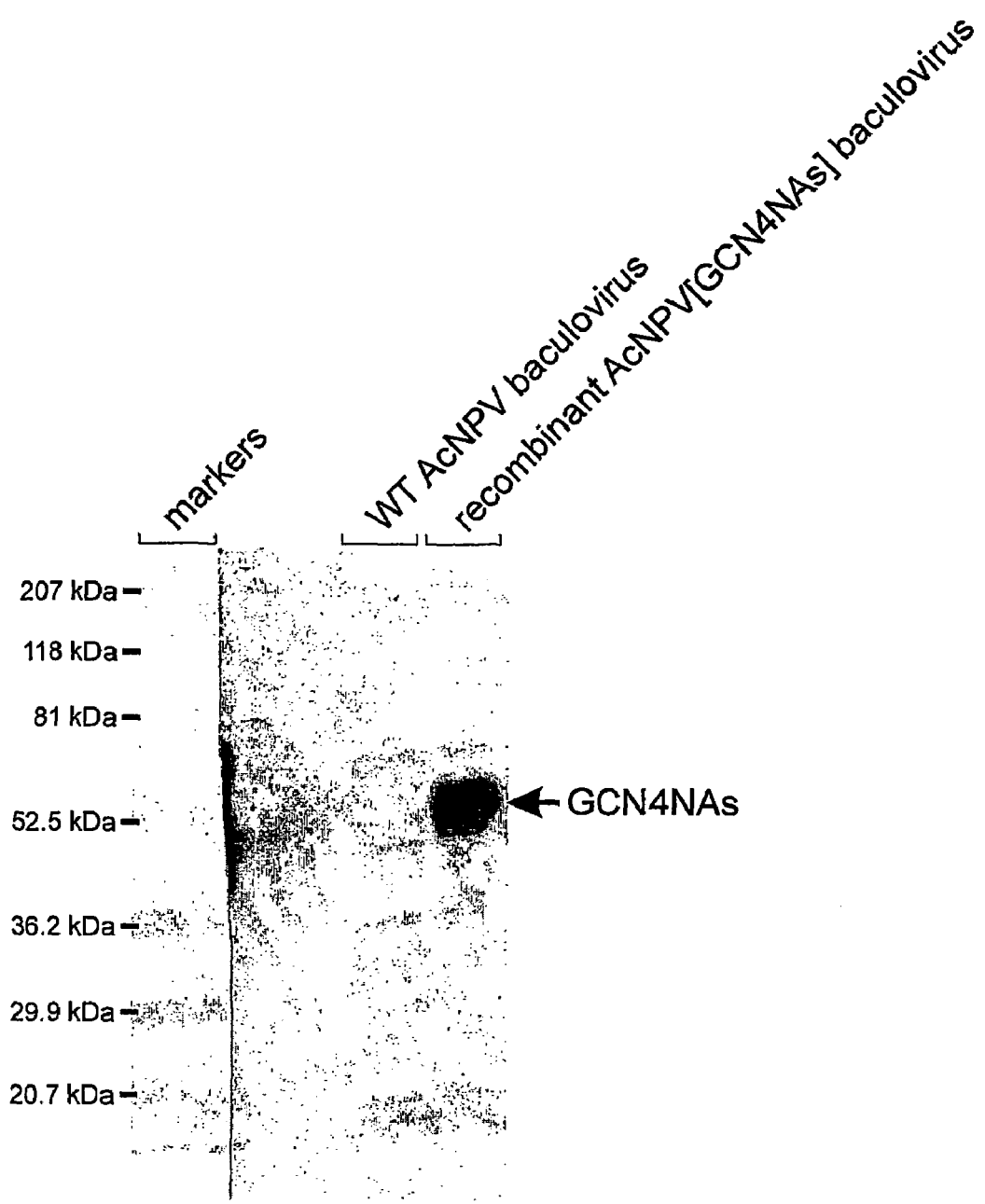

FIG. 6: Analysis of GCN4NAs expression by Western blot.

Figure 7:
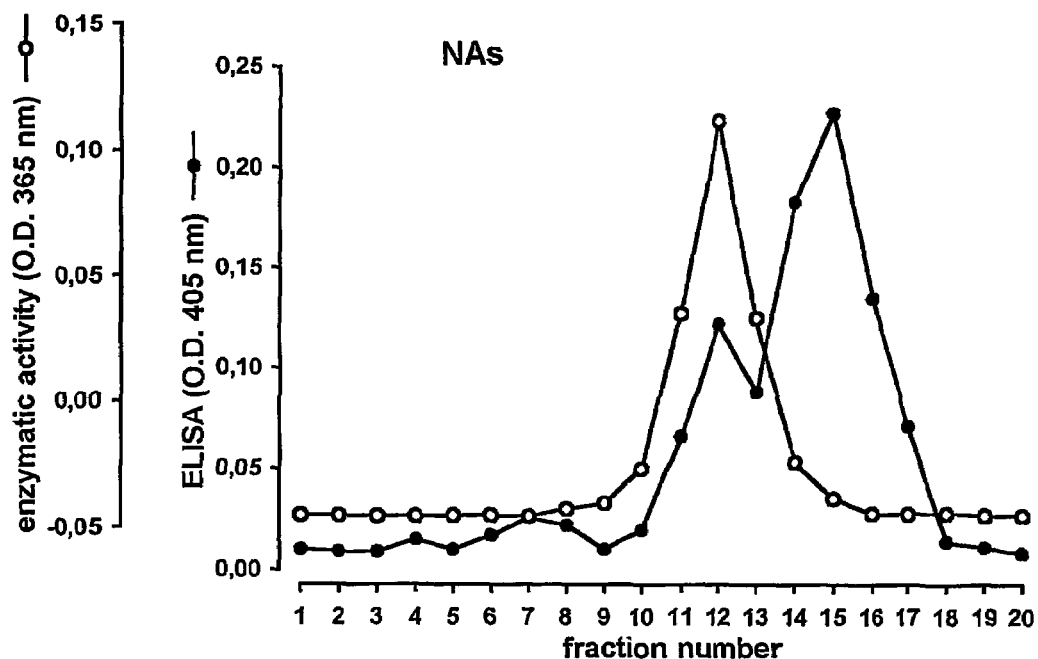
Figure 7:
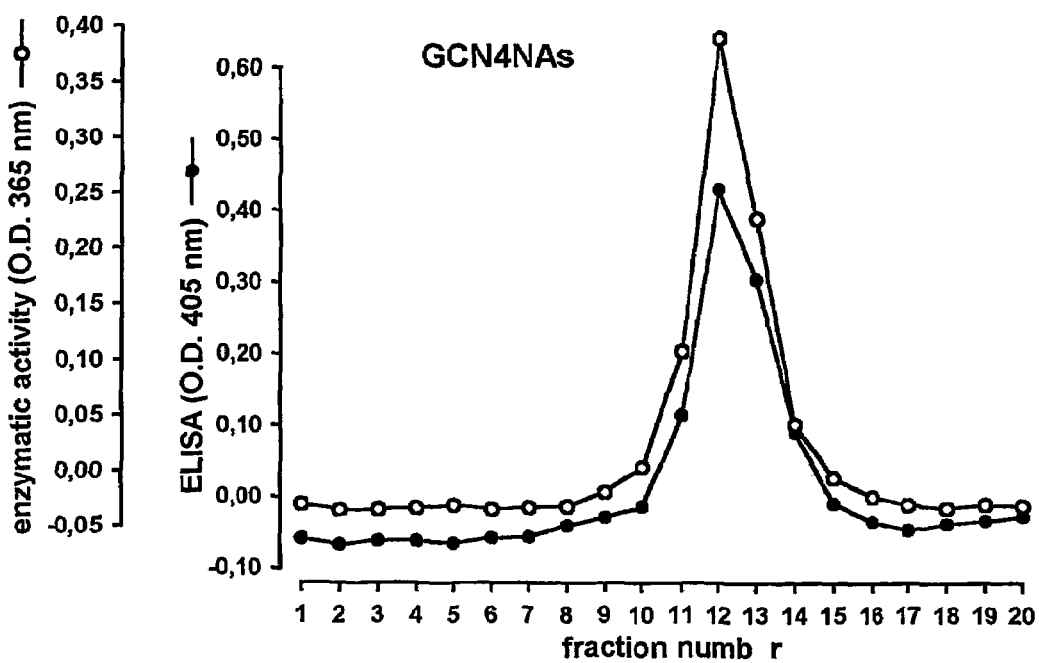

FIG. 7: Sucrose gradient pattern of secreted neuraminidase and secreted chimeric GCN4NAs.

Figure 8:
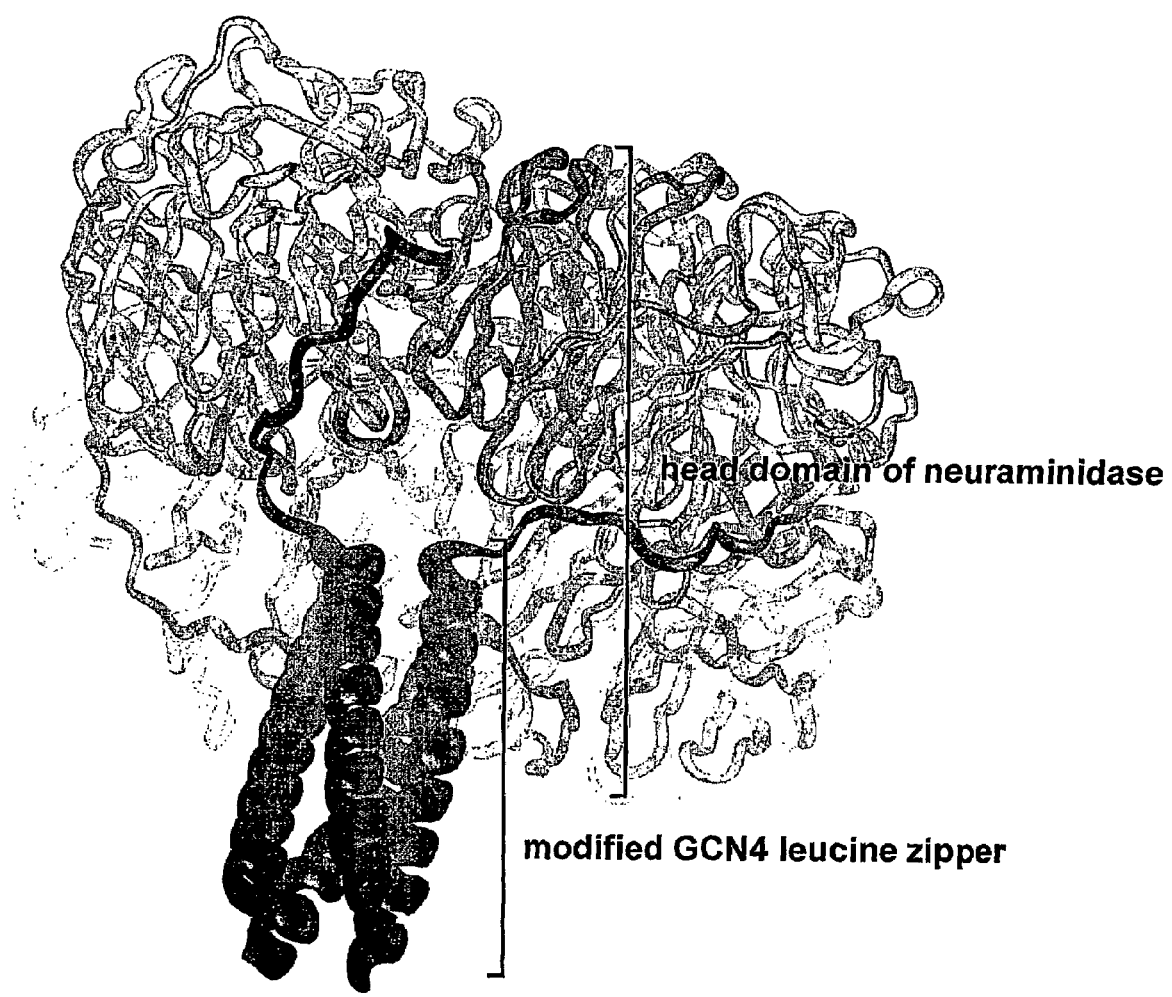

FIG. 8: Proposed structure of GCN4NAs based on the known structure of its two constituent domains.

Figure 9:
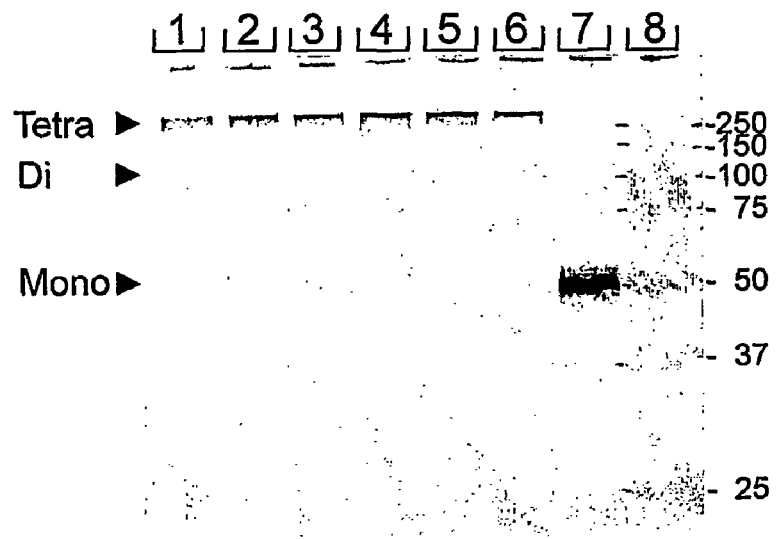

FIG. 9: GCN4NAs is a tetramer as shown by chemical cross-linking of its subunits.
Lane 1: 30 min incubation of GCN4NAs with 1.2 mM BS3
Lane 2: 5 min incubation of GCN4NAs with 1.2 mM BS3
Lane 3: 30 min incubation of GCN4NAs with 0.6 mM BS3
Lane 4: 5 min incubation of GCN4NAs with 0.6 mM BS3
Lane 5: 30 min incubation of GCN4NAs with 0.3 mM BS3
Lane 6: 5 min incubation of GCN4NAs with 0.3 mM BS3
Lane 7: GCN4NAs without cross-linker
Lane 8: MW FIG. 10: Characterisation of sM2eGCN4 expression.

Figure 11:
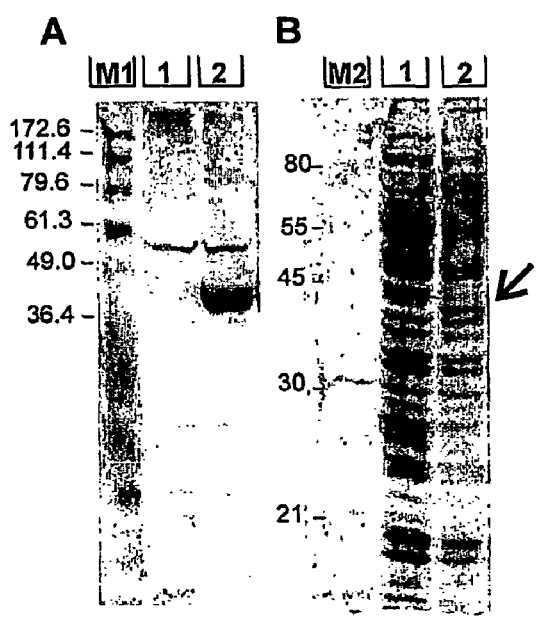

FIG. 11: Analysis by 12% SDS-PAGE of proteins secreted by baculovirus-infected Sf9 cells in TC100 medium. TCA precipitated proteins from 800μl medium were dissolved in loading buffer.

Lanes A1 and B1 were loaded with proteins derived from cells infected with baculovirus obtained by recombination with an empty expression vector. Lanes A2 and B2 were loaded with proteins derived from cells infected with baculovirus containing the genetic information for expression of sM2eGCN4C3d.

A: Detection by Western blot analysis using the monoclonal antibody 2C9 (Neirynck et al., 1999).

B: Proteins were stained with SyproOrange (Molecular Probes, Eugene, Oreg. USA). An arrow indicates the position of the recombinant protein sM2eGCN4C3d.

M1='Benchmark' prestained protein molecular weight markers (Gibco BRL, Bethesda, Md., USA). M2 =protein molecular weight markers from Molecular Probes (Eugene, Oreg., USA)

Figure 12:
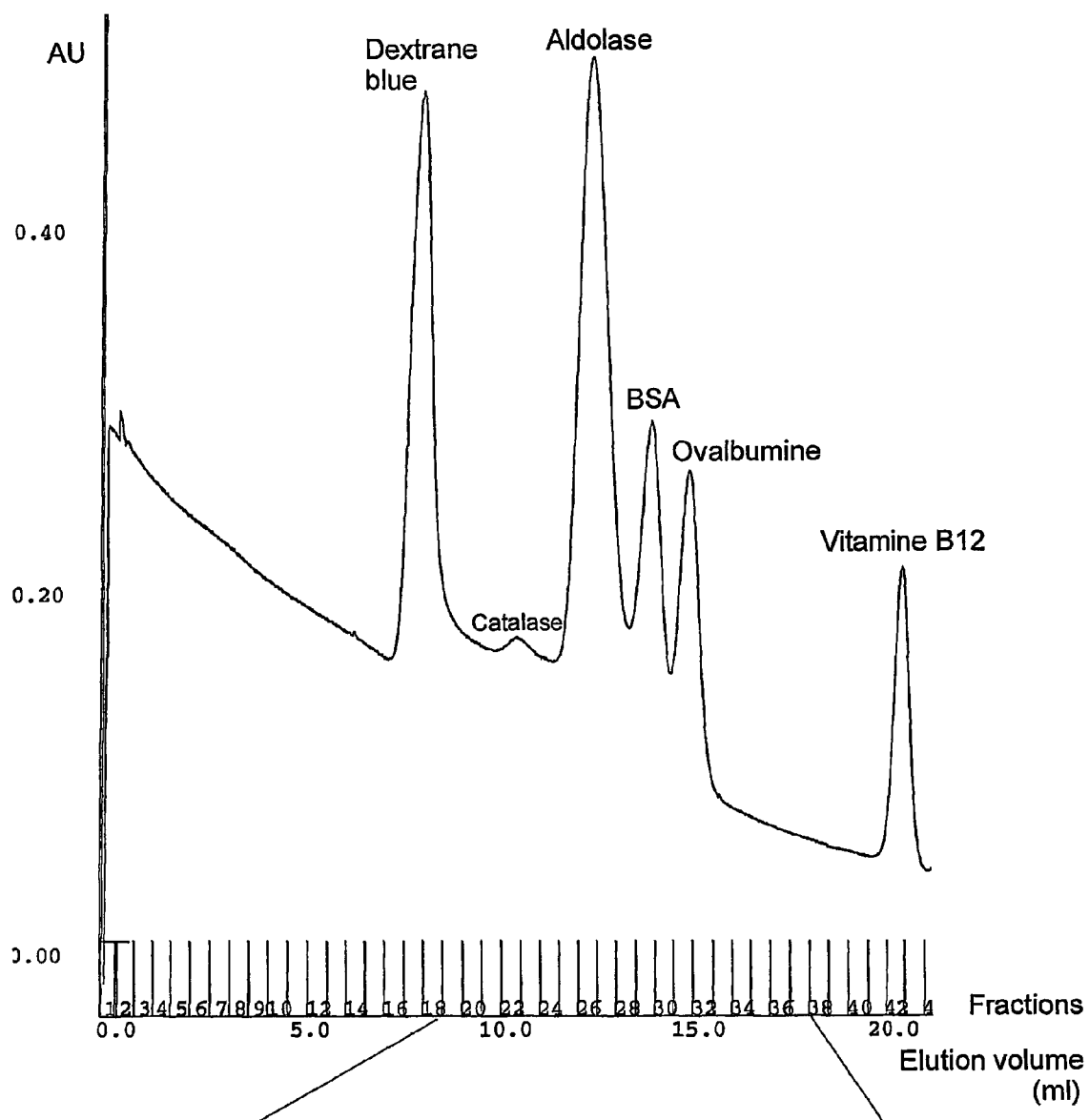

FIG. 12: Gel filtration chromatography on a Superdex 200 HR column (Amersham Pharmacia Biotech, Uppsala, Sweden).
(A) Elution profile after separation of a mixture of reference proteins for calibration.
(B) Elution profile of partially purified, recombinant sM2eGCN4C3d; fractions were analyzed by Western blot as described in the legend to FIG. 11.

Figure 13:
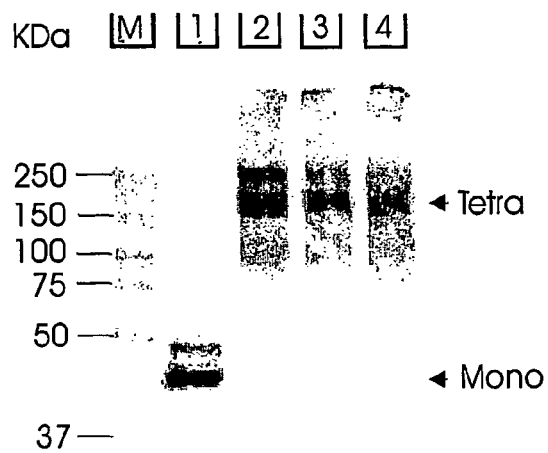

FIG. 13: sM2eGCN4C3d is a tetramer as shown by chemical cross-linking of its subunits.
Western blot analysis of sM2eGCN4C3d before (lane 1) and after treatment with 4, 6 and 12 mM cross-linking agent BS3 (lanes 2, 3 and 4, respectively). Proteins were denatured in Laemmli buffer in the presence of DTT as reducing agent, and separated on a 5-14% gradient SDS-polyacrylamide gel. Blotting of the proteins was followed by screening with anti-M2 monoclonal antibody 2C9, followed by secondary antibody (rat anti-mouse IgG-peroxidase conjugate; Sigma Chemical Company, St. Louis, Mo., USA). Positive signals were revealed after addition of "Renaissance" chemiluminescent substrate solution (NEN Life Science Products, Boston, Mass., USA).

Figure 14:
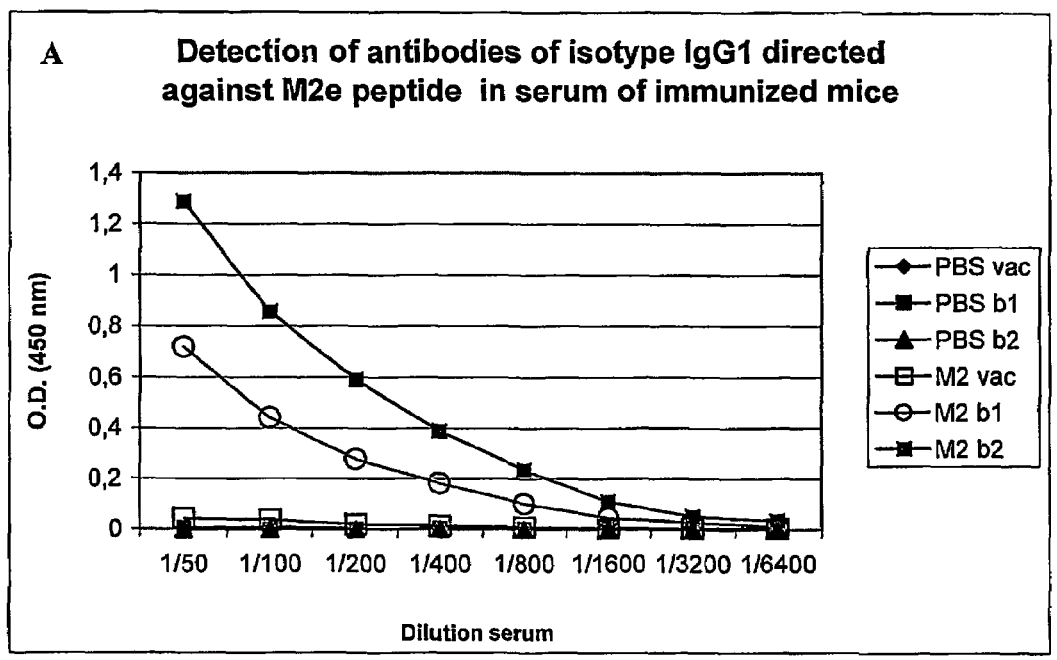
Figure 14:
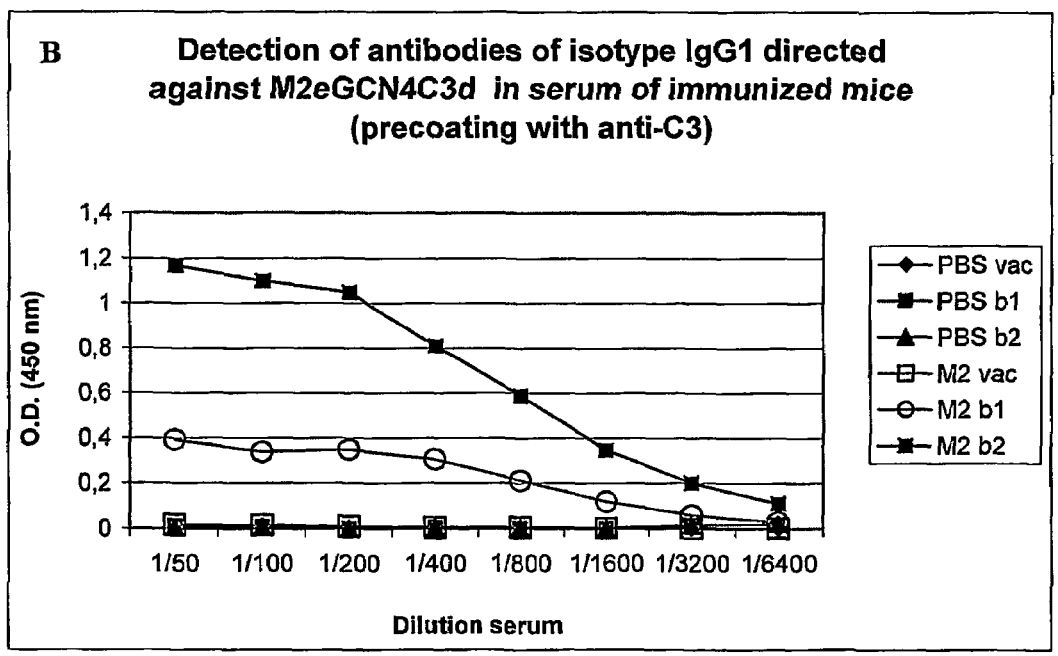
Figure 14:
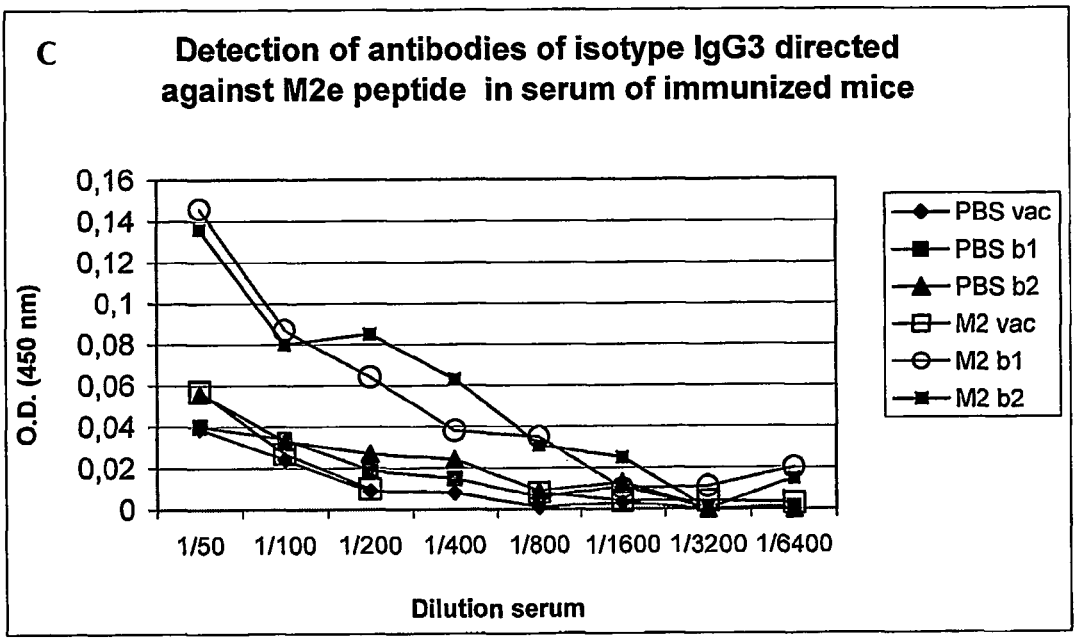
Figure 14:
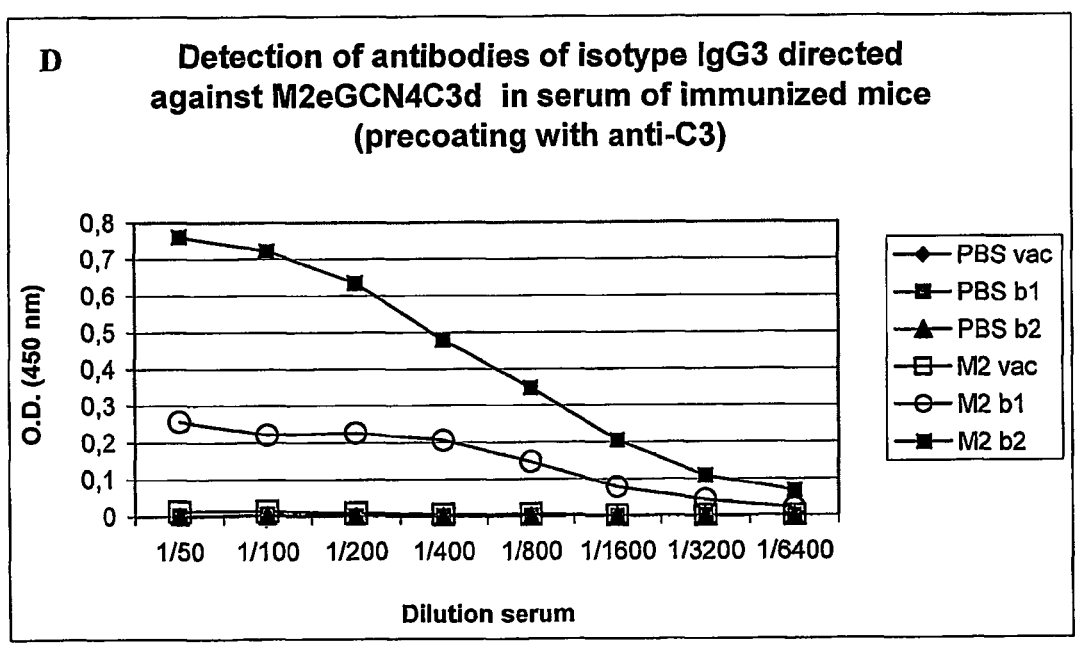

FIG. 14: Antibody response against sM2eGCN4C3d
Mice were injected i.p. either with PBS+adjuvant or sM2eGCN4C3d+adjuvant, and the injections were repeated twice at 2 weeks interval (cf. Example 13). Serum was taken 10 days after each injection, and antibody titers were determined using either M2e-peptide or sM2eGCN4C3d for trapping. Vac, b1 and b2: serum taken after first injection, first boost and second boost, respectively.

Figure 15:
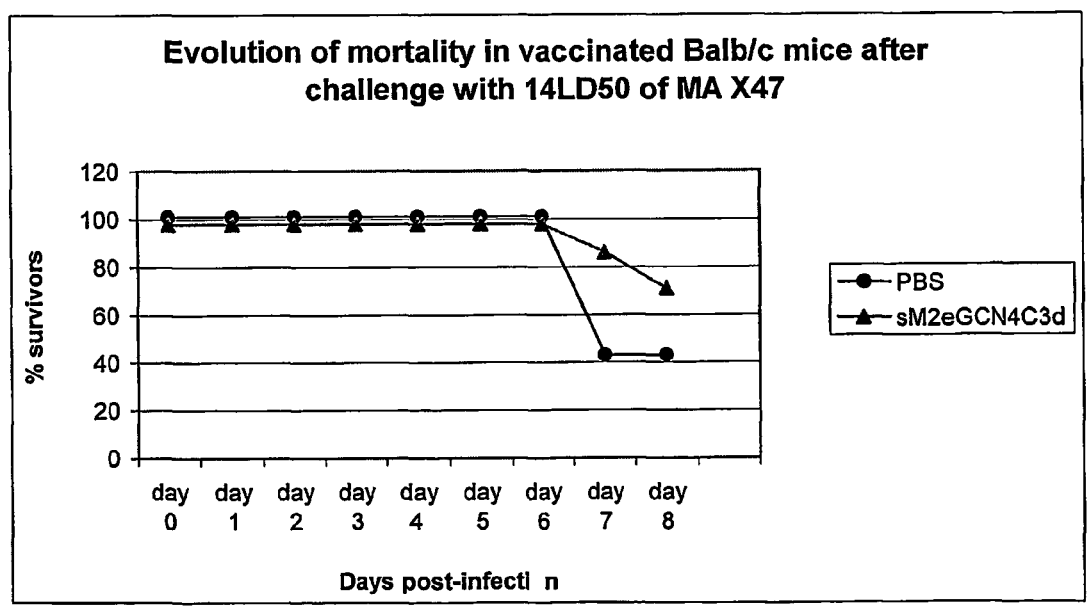

FIG. 15. Survival of mice after a challenge with mouse-adapted influenza virus

Balb/c mice were immunized three times with PBS or 10 μg sM2eGCN4C3d (cf. Example 13), and challenged with homologous, mouse-adapted X47 virus

EXAMPLES

Example 1

Construction fpACGCN4NAs

All PCR amplifications were carried out using Vent polymerase (New England Biolabs, Beverly, Mass., USA), with a total of 10 cycles and 200 ng plasmid for all reactions. The cycling conditions were as specified for the individual amplifications. The oligonucleotides used for the constructions are shown in Table 1.

The baculovirus transfer vector pAC2IVNAs (containing the cDNA sequence of the N2 neuraminidase of A/Victoria/3/75 influenza virus of which the membrane anchor was substituted by the cleavable signal sequence of the haemagglutinin; described in detail in Deroo et al., 1996) was used as a template to generate two PCR products using the primer pairs BACfor/GCN4nh (denaturation: 94° C., 1 min; annealing 57° C., 1 min; synthesis 75° C., 30 sec) and GCN4cooh/BACrev (denaturation: 94° C., 1 min; annealing 59° C., $_1$ min; synthesis 75° C., 2 min 30 sec), which were subsequently digested with PstI/HindIII and BcII/Xbal; respectively. The resulting fragments and a 5'end kinated synthetic DNA fragment (GCN4pos/GCN4neg complementary oligonucleotide pair) were then ligated with the PstI/Xbal 10089 bp vector fragment of pAC2IVNAs. The inserted sequence in the baculovirus transfer vector obtained in this way (pACGCN4NAs), codes for the antigenic and catalytic head domain of the neuraminidase (NA) preceded by a modified GCN4 leucine zipper which promotes the formation of a tetrameric protein (Harbury et al., 1993), and by the secretion signal of the influenza haemagglutinin (sHA). Expression of the fusion gene is controlled by the baculovirus polyhedrin promotor (Phprom). The corresponding recombinant baculovirus (designated AcNPV[GCN4NAs]) was generated by calcium phosphate cotransfection of Sf9 insect cells with BaculoGold baculovirus DNA (Pharmingen, San Diego, Calif., USA), following the procedure as described in King and Possee (1992). The construction is summarized in FIG. 1.

Example 2

Construction of pACsM2eGCN4

After PCR amplification of the baculovirus GP67 secretion signal (primers GP67s and GP67a; denaturation: 94° C., 1 min; annealing 62° C., 1 min; synthesis 75° C., 45 sec) out of pACGP67A (baculovirus transfer vector purchased from Pharmingen, San Diego, Calif., USA) and digestion with SpeI/HindIII, the fragment was subcloned in the SpeI/HindIII vector sequence of pUCC3d (described in example 3), resulting in pUCsgp. Following digestion of pUCsgp with HindIII/NaeI, the GP67 secretion signal was fused with the M2e fragment (coding for the ectodomain of the M2 protein) obtained by PCR amplification (primers M2Ss and UM2ECa; denaturation: 94° C., 1 min; annealing: 62° C., $_1$ min; synthesis: 75° C., 20 sec) and subsequent treatment with HindIII. This construct, referred to as pUCsgpM2e, was used as a template to generate a new PCR fragment (primers GP67s and M2rev; denaturation: 94° C., 1 min; annealing 56° C., 1 min; synthesis 75° C., 30 sec), which was digested with SpeI and BspEI. The GCN4 PCR fragment obtained from pACGCN4NAs (primers GCNfor and GCNrev; denaturation: 94° C., 1 min; annealing 58° C., 1 min; synthesis 75° C., 30 sec) was then ligated with the former fragment together with the SpeI/BgIII 9610 bp vector fragment of pACGP67A. In the resulting baculovirus transfer vector pACsM2eGCN4, the sequence coding for the M2 ectodomain (M2e) is fused at its C-terminus to a modified GCN4 leucine zipper which is able to induce tetramerization (Harbury et al., 1993), and is preceded by the GP67 secretion signal (sGP67), and by the polyhedrin promoter (Phprom). The corresponding recombinant baculovirus (designated AcNPV[sM2eGCN4]) was generated by calcium phosphate cotransfection of Sf9 insect cells with BaculoGold baculovirus DNA (Pharmingen, San Diego, Calif., USA), following the procedure as described in King and Possee (1992). The construction is summarized in FIG. 2.

Example 3

Construction of pACsM2eGCN4C3d

The plasmid pSG5.C3d3.YL (Dempsey et al, 1996) was a kind gift from Dr. D. T. Fearon, Department of Medicine, University of Cambridge School of Medicine, Cambridge, UK. The C3d genetic information was first amplified and subcloned in the vector pUC18 (Norrander et al., 1983) as follows: The C3d sequence was PCR amplified (primers C3ds and C3da, pSG5.C3d3.YL as template; denaturation: 94° C., 30 sec; annealing: 60° C., 20 sec; synthesis: 72° C., 2 min), followed by cleavage with SpeI and BgIII to allow insertion into SpeI/BgIII digested, intermediate vector pUC18f. The latter had been created by inserting a SpeI restriction site in SmaI opened pUC18, using the adaptor 5'TCACTAGTGA3', and by inserting a BgIII restriction site in the HindIII opened vector, using the adaptor 5'CAGATCTG3'. The result of cloning the PCR fragment in pUC18f was the plasmid pUCC3d. The starting plasmid pSG5.C3d3.YL was cleaved also with XbaI, followed by blunting with T4 DNA polymerase, and by subsequent digestion with BspEI, which provided a 680 bp fragment. The latter was inserted in the vector pUCC3d previously cleaved with SpeI, blunted with T4 DNA polymerase, and then cut with BspEI. The result was the plasmid pUCC3dEEF. Starting from the plasmid pACsM2eGCN4 (example 2) and using the primers GP67s and GCNrev2, the sM2eGCN4 coding sequence was PCR amplified (denaturation: 94° C., 1 min; annealing: 57° C., 1 min; synthesis: 75° C., 30 sec), and then treated with SpeI and BamHI. The resulting fragment was inserted into SpeI/BamHI digested pACGP67A (baculovirus transfer vector purchased from Pharmingen, San Diego, Calif., USA). This provided the intermediate construct pACsM2eGCN4f. The aforementioned plasmid pUCC3dEEF was digested with BgIII and EcoRI to provide a 1094 bp fragment coding for C3dEEF, which was subcloned in BamHI and EcoRI opened pACsM2eGCN4f. This provided the plasmid pACsM2eGCN4C3d. In this baculovirus transfer vector, the polyhedrin promotor (Phprom) is followed by a multi-component fusion gene coding for the GP67 secretion signal (sGP67), the M2e ectodomain (M2e), the GCN4 leucine zipper, the mouse C3d domain and a C-terminal 'EEF' tag. The corresponding baculovirus (designated AcNPV

Figure 1:
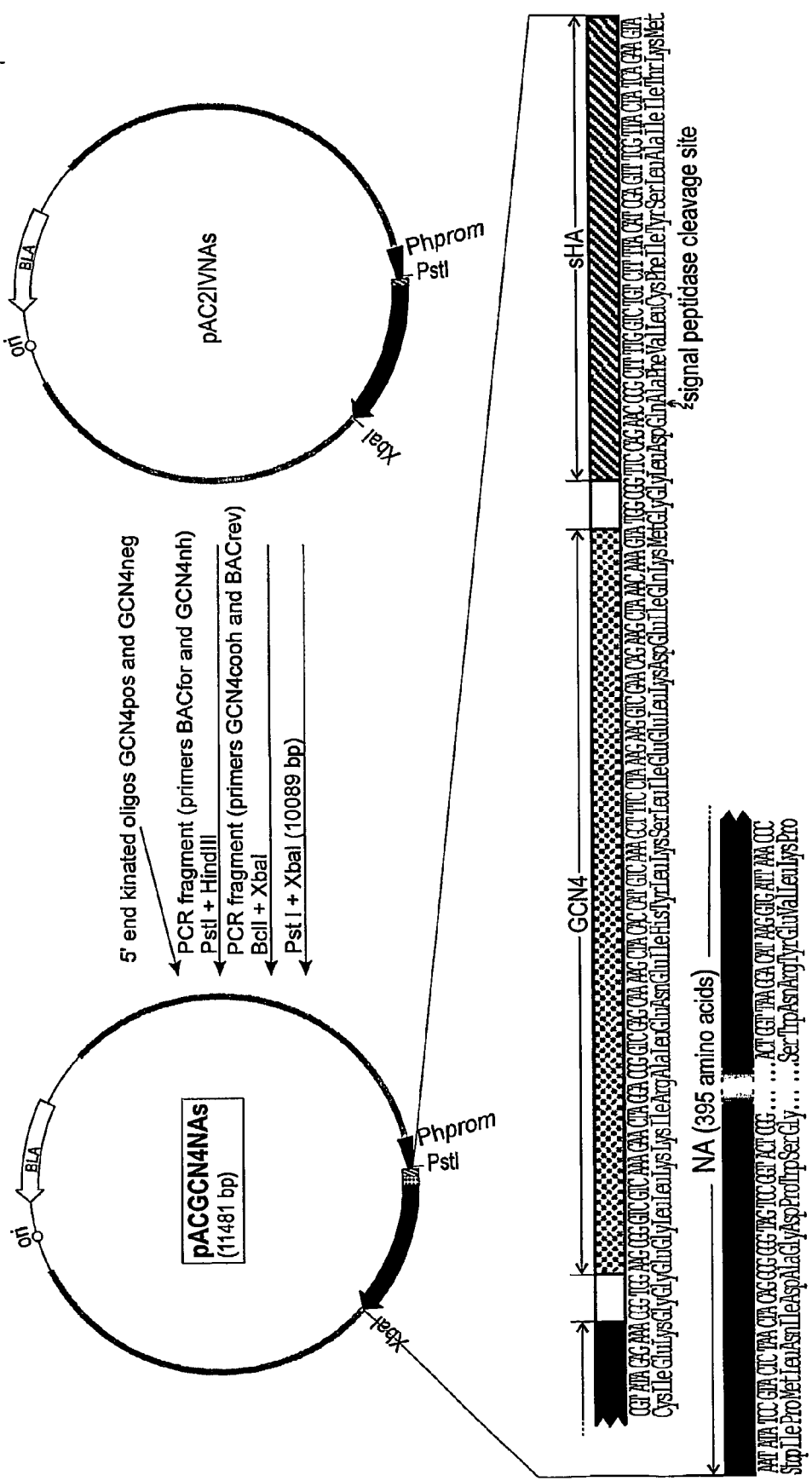
FIG. 1: Construction of pACGCN4NAs
Phprom: polyhedrin promoter
sHA: secretion signal of the influenza haemagglutinin
GCN4: modified GCN4 leucine zipper
NA: neuraminidase
bla: β-lactamase
ori: origin of replication
bold grey line: baculovirus homology region
Figure 2:
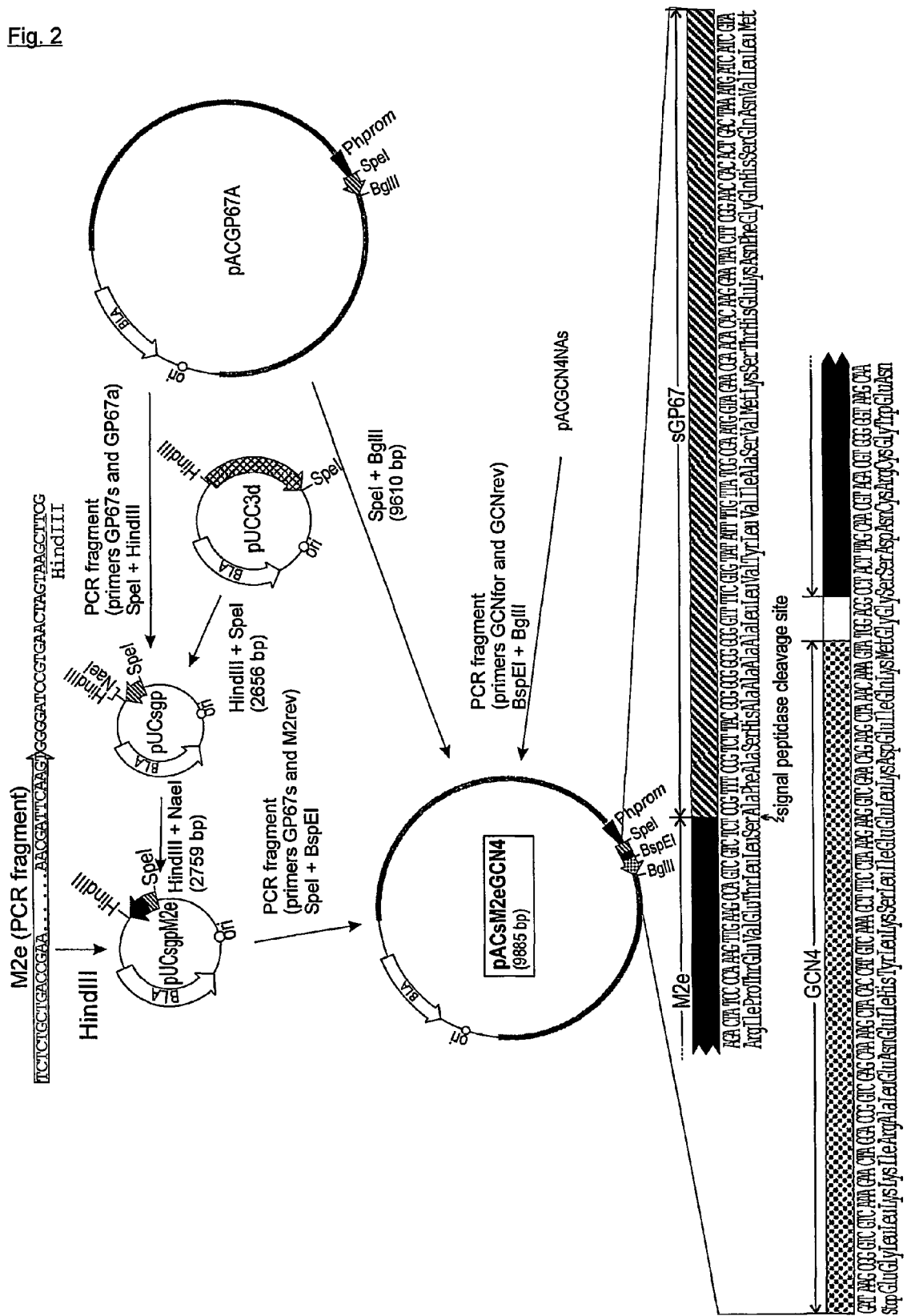
FIG. 2: Construction of pACsM2eGCN4
The sequence shown is SEQ ID NO:1, in reverse orientation.
Phprom: polyhedrin promoter
sGP67: secretion signal of the baculovirus GP67 protein
M2e: extracellular part of M2 (M2 ectodomain)
GCN4: modified GCN4 leucine zipper
bla: β-lactamase
ori: origin of replication
bold grey line: baculovirus homology region
The sequence shown is SEQ ID NO: 3, in reverse orientation.
Figure 3:
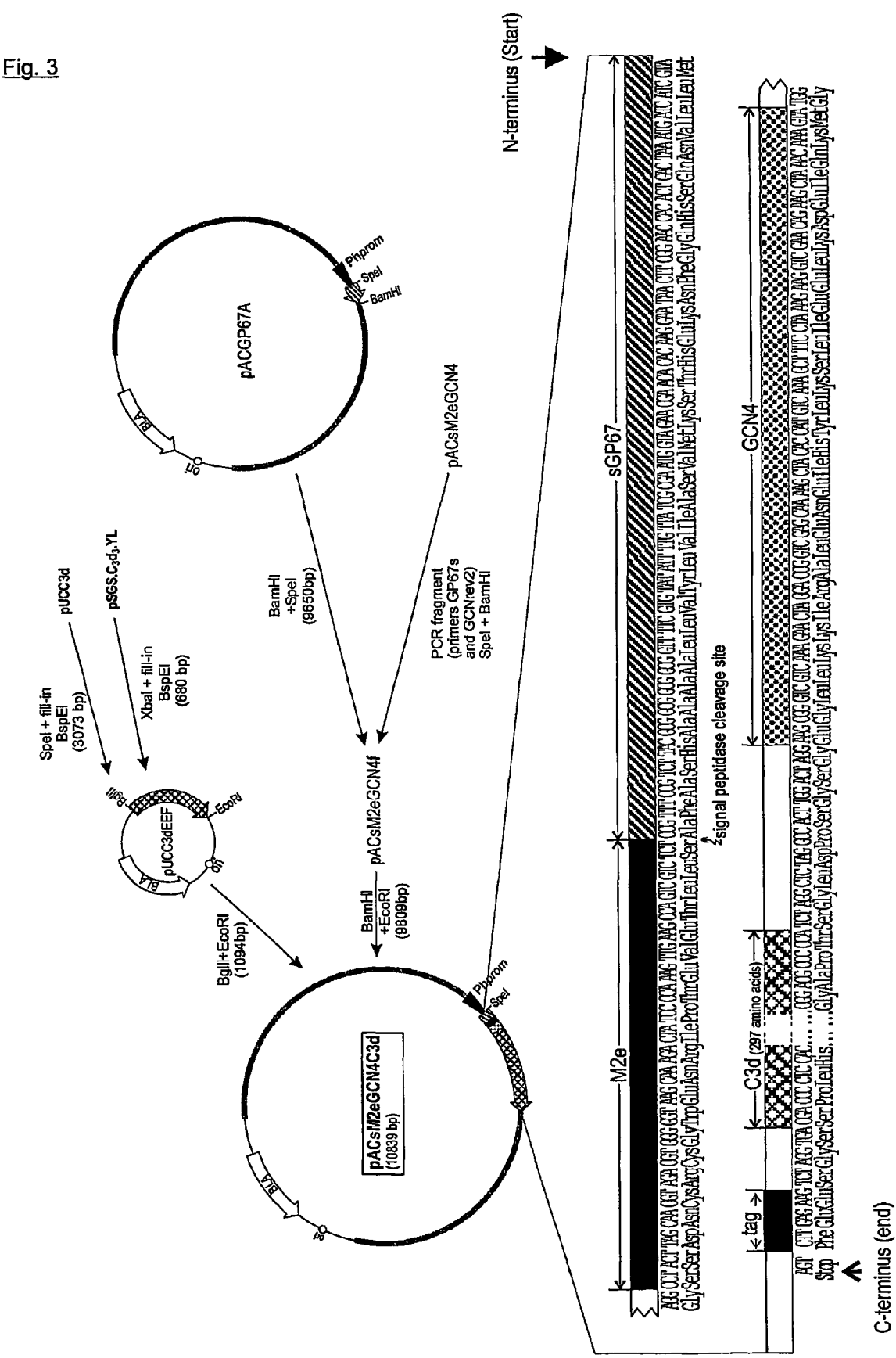
FIG. 3: Flow diagram for the construction of pACsM2eGCN4C3d. Only restriction sites relevant to the cloning procedure have been indicated.

[sM2eGCN4C3d]) was generated by calcium phosphate cotransfection of Sf9 insect cells with BaculoGold baculovirus DNA (Pharmingen, San Diego, Calif., USA), following the procedure as described in King and Possee (1992). The construction is summarized in FIG. 3.

Example 4

Analysis of Antibody Response Against Different Oligomeric Subforms of Purified Secreted Neuraminidase Secreted recombinant NA (NAs) was produced by a baculovirus expression system and subsequently purified according to Deroo et al. (1996). After Superdex 200 gel filtration, which is the final step of the purification procedure described in Deroo et al. (1996), the fractions corresponding to monomeric, dimeric and tetrameric NAs were pooled separately, and concentrated by ultrafiltration using Centriplus devices (10 kDa cut-off)(Amicon, Danvers, Mass., USA). Groups of 12 female Balb/c mice (SCK Mol, Belgium) were then immunized three times by subcutaneous injection with 1 µg of a specific oligomeric subform in the presence of a low-reactogenic adjuvant, as described in Deroo et al. (1996). Two weeks after each immunization, blood was collected from the tail vein and serum was prepared. Serum samples were subsequently analyzed by ELISA. For this purpose, 96-well plates were coated with purified, pronase-cleaved NA (Deroo et al., 1993), and incubated with 2-fold serum dilutions. Serum antibody titers were measured by adding alkaline phosphatase conjugated goat anti-[mouse IgG] antibody (Sigma Chemical Co., St. Louis, Mo., USA) and p-nitrophenyl phosphate (Sigma Chemical Co., St. Louis, Mo., USA) as a substrate. The serum antibody titer corresponds to the $\log_2$ value of the dilution factor which gave an OD of 0.5 above the control. Mice immunized with tetrameric NAs show a superior antibody respons throughout the immunization regimen (FIG. 4). After 2 immunizations, a ~17-fold difference was detected in favor of the mice immunized with tetrameric NAs as compared to those that received an equal dose of dimeric NAs, and a ~137-fold difference compared to the group immunized with an equal dose of monomeric NAs. The difference between tetrameric and monomeric vaccines increased even further after the third immunization, up to a factor of ~360.

Example 5

Survival of Mice Challenged with a Lethal Dose of Influenza Virus after Vaccination with Different Oligomeric Subforms of Purified, Secreted Neuraminidase Groups of 12 female Balb/c mice were immunized subcutaneously with different oligomeric subforms of purified, secreted neuraminidase (NAs), as outlined under example 4. Three weeks after the third injection, mice were challenged with a potentially lethal dose of mouse-adapted influenza virus (X47 reassortant strain) as described in Deroo et al. (1996). No lethality was observed among the animals that received tetrameric NAs vaccine. By contrast, only 75% and 50% of the animals immunized with dimeric and monomeric NAs, respectively, survived the challenge (FIG. 5).

Example 6

Analysis of GCN4NAs Expression by Western Blotting

Log-phase Sf9 insect cells were inoculated with the indicated baculovirus at high multiplicity of infection (>10). Cells were subsequently transferred to serum-free TC100 medium (Gibco BRL, Bethesda, Md., USA) and further incubated for 48 h before harvesting the supernatant. Proteins were precipitated by adding an equal volume of acetone (pre-equilibrated at −20° C.) and subsequently analysed by 12% reducing SDS-PAGE followed by Western blotting. Bands were visualized using a rabbit polyclonal IgG antibody against pronase-cleaved neuraminidase, followed by incubation with a secondary antibody (goat anti-[rabbit IgG]—alkaline phosphatase conjugate; Sigma Chemical Co., St. Louis, Mo., USA) and BCIP/NBT substrate solution. Secreted GCN4-fused neuraminidase (GCN4NAs), after denaturation, is clearly visible as a band of ~55 kDa (FIG. 6).

Example 7

Sucros Gradient C ntrifugation of NAs V rsus GCN4NAs

Secreted neuraminidase (NAs) and secreted GCN4-fused neuraminidase (GCN4NAs) were produced as outlined under example 4 by infection of Sf9 cells with the recombinant baculovirus described in Deroo et al. (1996) or with AcNPV [GCN4NAs], respectively. Harvested supernatant (10 ml) was concentrated using Centriplus devices (10 kDa cut-off) (Amicon, Danvers, Mass., USA) until ~1 ml, and subsequently supplemented with 1 volume of 100 mM Tris.Cl pH7.4, 200 mM NaCl, 0.2% Triton X-100, containing a protease inhibitor cocktail (Complete, Roche Molecular Biochemicals, Basel, Switzerland). Alternatively, when working with large volumes of harvested supernatant (200 ml), GCN4NAs was precipitated with ammonium sulfate. Material precipitating between 60% and 80% $(NH_4)_2SO_4$ saturation, was collected by centrifugation (10000 g, 60 min) and dissolved in 50 mM Tris.Cl pH7.4, 100 mM NaCl, 0.2% Triton X-100 containing a protease inhibitor cocktail (Complete, Roche Molecular Biochemicals, Basel, Switzerland). This solution containing GCN4NAs was dialysed against the same buffer.

After centrifugation to remove insoluble components (10 min at 14000 rpm), 1 ml sample was loaded on a 30 ml continuous sucrose gradient (5%-25%) made up in 10 mM Tris.Cl pH 7.4, 100 mM NaCl, 0.1% Triton X-100, and supplemented with Complete protease inhibitors. Gradients were centrifuged at 10° C. in a SW28 Beckman rotor for 16 h at 28000 rpm. Fractions of 1.5 ml were then collected from the bottom of the gradient and analysed by ELISA and by enzymatic activity. ELISA was carried out in 96-well plates coated with a rabbit IgG fraction raised against purified, pronase-cleaved neuraminidase (cf. example 6). Gradient fractions were added to the plates, and bound NAs was detected by addition of biotin-conjugated, anti-pronase-cleaved NA rabbit IgG. Plates were developed by incubating them with streptavidin-alkaline phophatase conjugate (Gibco BRL, Bethesda, Md., USA) and p-nitrophenyl phosphate as a substrate. OD values were read at 405 nm. Analysis of enzymatic activity was performed as described in Deroo et al. (1996). The profile obtained with NAs following sucrose gradient centrifugation is in agreement with the gel filtration profile of purified NAs described in Deroo et al. (1996), and typically results in two major peaks corresponding to catalytically active, tetrameric NAs, and catalytically non-active, dimeric NAs, respectively, the latter form representing about ⅔ of the total amount of secreted NAs (FIG. 7). The amount of monomeric NAs was below detection levels in this experimental set-up. By contrast, GCN4NAs was completely secreted as a catalytically active, tetrameric protein, with no detectable amounts of oligomeric forms of lower order. Its sedimentation at the same rate as recombinant, tetrameric NAs indicates a similar molecular mass. The relative specific enzymatic activities of the sucrose gradient purified proteins are compared in Table II. A model of the recombinant tetrameric protein complex is shown in FIG. 8.

Example 8

Characterisation of GCN4NAs by Cross-Linking

Samples of partially purified GCN4NAs obtained by sucrose gradient centrifugation, as describes in example 7, were concentrated using Microcon devices (10 kDa cut-off) (Amicon, Danvers, Mass., USA) and dialysed using Spectra/Por SispoDialyzer (8 kDa cut-off) (Spectrum, Rancho Dominguez, Calif., USA) overnight against PBS to remove Tris buffer. Cross-linkers were obtained from Pierce (Rockford, Ill., USA). Bis(sulfosuccinimidyl)suberate (BS3) was added from a freshly made 20 mM stock solution in DMSO to final concentrations of 2 to 6 mM. The reactions were incubated for 1 hour at room temperature, and quenched for 15 minutes by addition of Tris buffer, pH 8, to a final concentration of 300 mM. After cross-linking, an equal volume of 2 ×SDS loading buffer (5% SDS, 100 mM DTT, 20% glycerol, 5 mM EDTA, 50 mM Tris buffer, pH 8) was added and the sample was boiled for 5 minutes. SDS PAGE analysis was carried out on a MiniProtean II apparatus (BioRad, Hercules, Calif., USA) using 4-15% precast gradient gels. Electroblotting from SDS PAGE gels onto nitrocellulose (NC) membranes was performed using a Mini Trans-Blot cell (BioRad, Hercules, Calif., USA) and required 45 min at 100 V. Thereafter, NC membranes were blocked in PBS containing 2% BSA for 2h. Blots were incubated with anti-NA rabbit serum (cf. example 6) diluted (1/5000) in PBS containing 1% BSA and 0.1% Tween-20 (PBT). After washing away unbound antibodies, alkaline phosphatase conjugated goat anti-rabbit-IgG serum (Organon Teknika, West Chester, Penn., USA) was added at a dilution of 1/7000 in PBT. Detection was achieved with NBT/BCIP (Roche Diagnostics, Indianapolis, Ind., USA). Prestained, broad range molecular weight marker (BioRad, Hercules, Calif., USA) was used for reference. Incubation of GCN4NAs in the presence of the cross-linker BS3 resulted in the formation of covalently linked oligomers, as depicted in FIG. 9. The major crosslinked species have an estimated molecular mass of 250 kDa and 115 kDa, corresponding to cross-linked tetramers and dimmers, respectively. The presence of the dimeric forms decreased with increasing concentration of cross-linker. This result confirms data obtained by sedimentation and by enzymatic activity, which all indicate that GCN4NAs exists in solution as a tetramer.

Example 9

Characterisation of sM2eGCN4 Expression

Log-phase Sf9 insect cells were inoculated with baculovirus AcNPV[sM2eGCN4] (example 2) or control virus at high multiplicity of infection (>10). Cells were subsequently transferred to serum-free TC100 medium (Gibco BRL, Bethesda, Md., USA) and further incubated for 48 h before harvesting the supernatant. Proteins were precipitated by adding an equal volume of acetone (pre-equilibrated at −20° C), dissolved in loading buffer and separated by 15% reducing SDS-PAGE, followed by Western blotting. Bands were visualized using the monoclonal antibody 2C9 directed against the M2e domain (Neirynck et al. 1999), followed by incubation with a secondary antibody (goat anti-[mouse IgG]—alkaline phosphatase conjugate; Sigma Chemical Co., St. Louis, Mo., USA) and BCIP/NBT substrate solution. Secreted GCN4-fused M2e (sM2eGCN4), after denaturation, was detected as a band of ~10.5 kDa (FIG. 10).

Example 10

Characterisation of sM2eGCN4C3d Expression

Log-phase Sf9 insect cells were inoculated with baculovirus AcNPV[sM2eGCN4C3d] (cf. example 3) or control virus ("mock infection") at high multiplicity of infection (>10). Cells were subsequently transferred to serum-free TC100 medium (Gibco BRL, Bethesda, Md., USA) and further incubated for 48 h before harvesting the supernatant. Proteins were analyzed by precipitation with ice-cooled TCA and subsequently separated by 12% reducing SDS-PAGE, followed by SyproOrange staining (Molecular Probes, Eugene, Oreg., USA). Secreted sM2eGCN4C3d was revealed as a band of ~41 kDa, which was not present in the medium of 'mock' infected Sf9 cells (FIG. 11). For 'mock' infection, baculovirus has been generated by calcium phosphate cotransfection of Sf9 cells with transfer vector pACGP67A without an insert for expression, and BaculoGold baculovirus DNA (Pharmingen, San Diego, Calif., USA), following the procedure as described in King and Possee (1992).

By Western blotting, sM2eGCN4C3d was again visualized as a band of ~41 kDa using the anti-M2e monoclonal antibody 2C9 (Neirynck et al., 1999), followed by incubation with a secondary antibody (rat anti-[mouse IgG]—peroxidase conjugate; Sigma Chemical Co., St. Louis, Mo., USA) and 'Renaissance' chemiluminescent substrate solution (NEN Life Science Products, Boston, Mass., USA). The same band was detected when rat monoclonal antibody YL 1/2 against the 'EEF' tag (Abcam Ltd, Cambridge, UK) was used, or sheep polyclonal antibody against mouse complement 3 (Biogenesis, Poole, UK). The following secondary antibodies were used: mouse monoclonal anti-rat kappa and lambda light chains (clones RT-39 & RL-6) conjugated with alkaline phosphatase, and donkey anti-sheep IgG conjugated with alkaline phosphatase, respectively (Sigma, St. Louis, Mo., USA).

For further characterization, the blotted proteins were stained with amido black, the ~41 kDa band was isolated by cutting the membrane, and N-terminal sequence analysis was carried out according to Bauw et al. (1987). The first four amino acids were identified as serine, leucine, leucine and threonine, respectively. This result demonstrates that cleavage of the GP67 signal sequence has been executed correctly, and confirms that the ~41 kDa band is without doubt sM2eGCN4C3d.

Example 11

Characterization of the Oligomeric Status of sM2eGCN4C3d

Secreted, recombinant sM2eGCN4C3d was produced by a baculovirus expression system, as described in example 10.

The following purification steps, summarized in Table III, were carried out: First, crude medium was fractionated by differential ammonium sulphate precipitation. Ammonium sulphate was added to the medium, cooled on ice, until 45% saturation and precipitated proteins were removed by centrifugation (Sorvall rotor SS34, 1 hour at 15000 rpm, 4° C.). The $(NH_4)_2SO_4$ concentration was raised to 95% saturation, and the resulting precipitate was collected by centrifugation. The pellet was redisolved in 50 mM Tris.Cl buffer, pH 7.2, (approximately ½₀th of the original volume of the medium), and desalted over a HiPrep Sephadex G25 column (Amersham Pharmacia Biotech, Uppsala, Sweden) equilibrated in 50 mM Tris.Cl, pH 7.2. The desalted protein solution was loaded on a Q-Sepharose FF column (h: 9 cm, d: 1.5 cm; Amersham Pharmacia Biotech, Uppsala, Sweden) equilibrated in 50 mM Tris buffer, pH 7.2, and elution was by a salt gradient of 200 to 400 mM NaCl in 20 mM Tris buffer, pH 7.2. A 100 μl aliquot of each fraction was used for analysis: Proteins were precipitated by TCA from 100 μl aliquots from each fractions in preparation for analysis by 12% SDS-PAGE followed by Western blotting and screening with the anti-M2e monoclonal antibody 2C9 (Neirynck et al., 1999), (cf. example 9), using as secondary antibody (rat anti-[mouse IgG]—peroxidase conjugate; Sigma chemical Co., St. Louis, Mo., USA) and 'Renaissance' chemiluminescent substrate solution (NEN Life Science Products, Boston, Mass., USA). Positive fractions were pooled, and the solution was concentrated using Vivaspin-30 and Centricon-100 ultrafiltration devices (Millipore Corporation, Bedford, Mass., USA).

Approximately 99% of the recombinant protein was retained by the Centricon-100 membrane, suggesting that the molecular mass of the sM2eGCN4C3d oligomer was higher than 100 kDa, as expected for a tetramer.

To verify further the oligomeric status of sM2eGCN4C3d, 150 μl of the concentrated, partially purified recombinant protein was loaded on a Superdex 200 HR gel filtration column (Amersham Pharmacia Biotech, Uppsala, Sweden), equilibrated in PBS, and resolved at a flow rate of 0.4 ml/min. This Superdex 200 column had previously been calibrated using a mixture of highly purified proteins (HMW and LMW calibration kits (Amersham Pharmacia Biotech, Uppsala, Sweden). As shown in FIG. 12, sM2eGCN4C3d was detected only in fractions nearly coinciding with those of aldolase (theoretical molecular mass 179 kDa), as can be expected for tetrameric sM2eGCN4C3d.

Example 12

Characterization of the Oligomeric Status of sM2eGCN4C3d by Cross-Linking

Samples (10 μl) of partially purified sM2eGCN4C3d (approx. 0.5 μg, in PBS; cf. example 11) were incubated with cross-linker BS3 (Pierce, Rockford, Ill., USA) at final concentrations of 4 to 12 mM. The cross-linker was added from a freshly made 40 mM stock solution in DMSO. The reactions were incubated for 10 minutes at room temperature, and quenched for 15 minutes by addition of 1 M Tris buffer, pH 7.5, to a final concentration of 300 mM. After incubation, an equal volume of 2×SDS loading buffer (5% SDS, 100 mM DTT, 20% glycerol, 5 mM EDTA, 50 mM Tris buffer, pH 8) was added and the samples were boiled for 5 minutes. SDS-PAGE analysis was carried out on a MiniProtean II apparatus (BioRad, Hercules, Calif., USA) using 4-15% precast gradient gels. Electroblotting from SDS-PAGE gels onto nitrocellulose (NC) membranes was performed using a Mini Trans-Blot cell (BioRad, Hercules, Calif., USA) and required 1 hour at 100 V. Thereafter, NC membranes were blocked overnight at 4° C. in PBS containing 2% BSA. Blots were incubated with anti-M2e monoclonal antibody 2C9 in TBS-T (50 mM Tris buffer, pH 7.0, 50 mM NaCl, and 0.1% Tween-20). After washing away unbound antibodies, the blot was screened with secondary antibody (rat anti-[mouse IgG]—peroxidase conjugate; Sigma chemical Co., St. Louis, Mo., USA) and positive signals were revealed after addition of 'Renaissance' chemiluminescent substrate solution (NEN Life Science Products, Boston, Mass., USA). Prestained broad range molecular weight marker proteins (BioRad, Hercules, Calif., USA) were used as references. As shown in FIG. 13, treatment of sM2eGCN4C3d with the cross-linker BS3 resulted in the formation of covalently linked oligomers. The major cross-linked species has an estimated molecular mass of approximately 164 kDa, while the monomer had a molecular mass of approximately 41 kDa. This result confirms data obtained by ultrafiltration and gelfiltration, which all indicate that sM2eGCN4C3d exists in solution as a tetramer.

Example 13

Analysis of the In Vivo Antibody Response against sM2eGCN4C3d

Secreted, recombinant sM2eGCN4C3d was produced by a baculovirus expression system and purified, as outlined in examples 10 and 11. Fractions containing recombinant protein were concentrated using Vivaspin-30 and Centricon-100 ultrafiltration devices (Millipore Corporation, Bedford, Mass., USA). In order to bring sM2eGCN4C3d in PBSA buffer (171 mM NaCl, 3.4 mM KCl, 10 mM $Na_2HPO_4$, 1.8 mM $KH_2PO_4$), the latter buffer was added to the concentrated protein solution (~200 μl) to bring the volume of the sample to 2 ml, after which the solution was concentrated again (~10-fold) using Centricon-100. This step was repeated twice. Groups of 7 female Balb/c mice (Charles River Laboratories, Sulzfeld Germany) at the age of 8 weeks were immunized by intraperitoneal injection with 10 μg sM2eGCN4C3d in the presence of Ribi adjuvant (25 μg monophosphoryl lipid A and 25 μg trehalose-6,6-dimycolate; cf. Neirynck et al., 1999) per mouse. Control mice received adjuvant dispersed in phosphate-buffered saline. The animals were housed in a temperature-controlled environment with 12 h light/dark cycles, and received food and water ad libitum. Two booster injections were given at two-week intervals by supplementing 10 μg sM2eGCN4C3d with 25 μg monophosphoryl lipid A and 25μg adjuvant peptide (cf. Neirynck et al., 1999) per mouse. Ten days after each immunization, blood was collected from the tail vein and serum was prepared. Serum samples were subsequently analysed by ELISA. For this purpose, 96-well plates were coated overnight at 37° C. with 50 μl of 2 μg/ml M2e peptide in 50 mM sodium bicarbonate buffer, pH 9.7, and then blocked with 200 μl PBS containing 1% BSA during 1 hour. Alternatively, 96-well plates were coated overnight at 4° C. with 50 μl of 10 μg/ml anti-mouse complement 3 polyclonal antibodies (ab3163, Biogenesis Ltd, Poole, UK) and blocked with 150 μl PBS containing 1% BSA during 1 hour. With the latter coating, capturing of sM2eGCN4C3d from insect cell medium was allowed during 1 hour 30 minutes at room temperature. After washing, a series of 1/2 dilutions of the different serum samples, starting with a 1/50 dilution, were loaded on peptide-or sM2eGCN4C3d protein coated wells. Bound antibodies were detected with a peroxidase-labeled antibody directed against mouse IgG1 and IgG3 (Southern Biotechnology Associates, Inc.), respectively, diluted 1/6000 in PBS containing 1% BSA and 0.05% Tween-20. After washing, the microtiter plates were incubated for 20 minutes with 3,3',5,5'-tetramethylbenzidine liquid substrate for peroxidase (Sigma, St. Louis, Mo., USA). The reaction was stopped by addition of 1 M $H_3PO_4$ and the absorbance at 450 nm was measured. To obtain the value for the specific reactivity to M2e, the absorbance obtained for pre-immune serum at a given dilution was substracted from the absorbance of post-vaccination and post-boosting sera of the corresponding dilution. As presented in FIGS. 14A and C, anti-M2e antibodies of isotypes IgG1 and IgG3 were induced in vaccinated and boosted mice. As shown in FIGS. 14B and D, similar profiles of antibody responses were obtained when recombinant sM2eGCN4C3d proteins were screened with antisera from vaccinated and boosted mice. Hence, it can be concluded that sM2eGCN4C3d can efficiently induce an antigenic antibody response in mice.

Example 14

Protection of Mice Challenged with a Lethal Dose of Influenza Virus after Vaccination with sM2eGCN4C3d Groups of 7 female pathogen-free Balb/c mice (Charles River Laboratories Sulzfeld, Germany) were immunized intraperitoneal with sM2eGCN4C3d, as described in example 13. Two weeks after the last immunisation, the mice were challenged intranasally with 14 $LD_{50}$ of mouse-adapted (m.a.) X47 (Neirynck et al., 1999). As presented in FIG. 15, sM2eGCN4C3d vaccinees were protected against a lethal dose of homologous m.a. influenza A virus.

TABLE I

PCR Primers and c mplem ntary oligonucle tid pair
PCR primers

BACfor:
5' TTTACTGTTTTCGTAACAGTTTTG 3'

GCN4nh:
5' TACAGAAGCTTGTCTTCGATTTGTTTCATACCGCCAAGGTCTTGGGC
GAAAACC 3'

GCN4cooh:
5' ATCTGATCAAGAAACTGCTGGGCGAAGGTGGCAAAGAGATATGCCCC
AAATTAG 3'

BACrev:
5' CATTTTATGTTTCAGGTTCAGGG 3'

GP67s:
5' GCTACTAGTAAATCAGTCACACCAA 3'

GP67a:
5' CGAAGCTTGCCGGCAAAGGCAGAATGCGCCGCC 3'

M2rev:
5' ACCATTCCGGATGAATCGTTGCATCTGCAC 3'

M2Ss:
5' TCTCTGCTGACCGAAGTTGAAAC 3'

UM2ECa:
5' CGAAGCTTACTAGTTCACGGATCCCCACTTGAATCGTTGCATCTGCA
CCC 3'

GCN4for:
5' AGATTTCCGGAGGTATGAAACAAATCGAAGAC 3'

GCN4rev:
5' ATAGGAGATCTATTCGCCCAGCAGTTTCTTG 3'

GCNrev2:

TABLE I-continued

5' TATTGGATCCGGTGAACCTGATCCTTCGCCCAGCAGTTTCTTG 3'

C3ds:
5' CCGCGCCCACCCGACGAGATCTCGGATCTACCCCC 3'

C3da:
5' GCACTAGTTCAAGGATCCGATCCGAACTCTTCAGATCC 3' c mplementary oligonucle tid pair

GCN4pos:
5' AGCTGGAAGAAATCCTTTCGAAACTGTACCACATCGAAAACGAGCTG
GCCAG 3'

GCN4neg:
5' GATCCTGGCCAGCTCGTTTTCGATGTGGTACAGTTTCGAAAGGATTT
CTTCC 3'

TABLE II

Estimated relative values of the specific activities of (tetrameric) NAs versus GCN4NAs

|        | tetrameric | dimeric    | monomeric  |
|--------|------------|------------|------------|
| NAs    | 100%       | non-active | non-active |
| GCN4NAs| >70%       |            |            |

The peak values of the enzymatic activity and the ELISA read-out obtained after sucrose gradient centrifugation were used to deduce a rough estimation of the relative specific activities. The specific enzymatic activity of GCN4NAs amounts to at least 70% of that of the tetrameric form of the unfused NAs protein.

TABLE III

Purification of sM2eGCN4C3d

| Steps | Volume (ml) | Protein (mg) | sM2eGCN4C3d (mg) | Yield (%) | Purification (-fold) |
|---|---|---|---|---|---|
| Crude medium | 1200 | 180 | 2.4 | 100 | 1.0 |
| 45-95% $(NH_4)_2SO_4$ precipitate | 48 | 58 | 1.9 | 79 | 2.5 |
| Sepharose Q | 30 | 6.5 | 0.9 | 37 | 11 |
| Superdex 200 | 6 | 1.2 | 0.6 | 17 | 38 |

References

Bauw, G., De Loose, M., Inze, D., Van Montagu, M. and Vandekerckhove, J. (1987) Alternations in the phenotype of plant cell studied by N-terminal amino acid sequence analysis of proteins electroblotted from two-dimensional gel-separated total extracts. *Proc. Natl. Acad. Sci. USA*, 84, 4806-4810.

Bucher, D. J. and Kilbourne, E. D. (1972). A2 (N2) neuraminidase of the X-7 influenza recombinant: determination of molecular size and subunit composition of the active unit. *J Virol*, 10, 60-66.

Burton, D. R. (1997). A vaccine for HIV type 1: the antibody perspective. *Proc. Natl. Acad. Sci. USA*, 94,10018-10023.

Chang, Z., Primm, T. P., Jakana, J., Lee, l. H., Serysheva, I., Chiu, W., Gilbert, H. F. and Quiocho, F. A. (1996) *Mycobacterium tuberculosis* 16-kDa Antigen (Hsp16.3) functions as an oligomeric structure in vitro to suppress thermal aggregation. *J Biol Chem*, 271, 7218-7223.

Dempsey, P. W., Allison M. E. D., Akkaraju, S., Goodnow, C. C., Fearon, D. T. (1996 C3d of complement as molecular adjuvant: bridging innate and acquired immunity. Science, 271, 348-350.

Deroo, T., Min Jou, W. And Fiers, W. (1996). Recombinant neuraminidase protects against lethal influenza. Vaccine 14, 561-569.

Domdey, H., Wiebauer, K., Kazmaier, M., Muller, V., Odink, K. and Fey, G. (1982) Characterization of the mRNA and cloned cDNA specifying the third component of mouse complement. *Proc. Natl. Acad. Sci.* USA, 79, 7619-7623

Harbury, P. B., Zhang, T., Kim, P. S. and Alber, T. (1993). A switch between two-, three-, and four-stranded coiled coils in GCN4 leucine zipper mutants. Science 262, 1401-1407.

King, L. A. and Possee, R. D. (1992). The baculovirus expression system. Chapman & Hall, University Press, Cambridge, UK.

Kodihalli, S., Justewicz, D. M., Gubareva, L. V. and Webster, R. G. (1995). Selection of a single amino acid substitution in the hemagglutinin molecule by chicken eggs can render influenza A virus (H3) candidate vaccine ineffective. *J Virol*, 69, 4888-4897.

Laver, W. G. and Valentine, R. C. (1969). Morphology of the isolated haemagglutinin and neuraminidase subunits of influenza virus. *Virology*, 38, 105-119.

Lin, X. H., Ali, M. A., Openshaw, H. and Cantin, E. M. (1996). Deletion of the carboxy-terminus of herpes simplex virus type 1 (HSV-1) glycoprotein B does not affect oligomerization, heparin-binding activity, or its ability to protect against HSV challenge. *Arch Virol*, 141, 1153-1165.

Lupas, A. (1996) Coiled coils: new structures and new functions. *TIBS* 21, 375-382.

Neirynck, S., Deroo, T., Saelens, X., Vanlandschoot, P., Min Jou, W. & Fiers, W. (1999) A universal influenza A vaccine based on the extracellular domain of the M2 protein. *Nature Medicine*, 5, 1157-1163.

Norrander J., Kempe T., & Messing, J. (1983) Construction of improved M13 vectors using oligodeoxynucleotide-directed mutagenesis. *Gene*, 26, 101-106.

O'Shea, E. K., Rutkowski, R. and Kim, P. S. (1989) Evidence that the leucine-zipper is a coiled coil. *Science*, 243, 538-542.

Ross, T. M., Xu, Y., Bright, R. A. and Robinson, H. L. (2000) C3d enhancement of antibodies to hemagglutinin accelerates protection against influenza virus challenge. *Nature Immunology*, 1(2), 127-131.

Sanchez, J., Johansson, S., Lowenadler, B, Svennerholm, A. M. and Holmgren, J. (1990). Recombinant cholera toxin B subunit and gene fusion proteins for oral vaccination. *Res Microbiol*, 141, 971-979.

Skinner, R. H., Bradley, S;, Brown, A. L., Johnson, N. J. E., Rhodes, S., Stammers, D. K. and Lowe, P. N. (1991) Use of the Glu-Glu-Phe C-terminal epitope for rapid purification of the catalytic domain of normal and mutant ras GTPase-activating proteins. *J. Biol Chem.*, 266, 14163-14166.

Sugrue, R. J. and Hay, A. J. (1991). Structural characteristics of the M2 protein of influenza A viruses: evidence that it forms a tetrameric channel. *Virology*, 180, 617-624.

Varghese, J. N., Laver, W. G. and Colman, P. M. (1983). Structure of the influenza virus glycoprotein antigen neuraminidase at 2,9 Å resolution. *Nature*, 303, 35-40.

Ward, C. W., Colman, P. M. and Laver, W. G. (1983). The disulphide bonds of an Asian influenza virus neuraminidase. *FEBS Lett*, 153, 29-30.

Winckler, G., Randolph, V. B., Cleaves, G. R., Ryan, T. E. and Stollar, V. (1988). Evidence that the mature form of the flavivirus nonstructural protein NS1 is a dimer. *Virology*, 162, 187-196.

The invention claimed is:

1. An oligomeric chimeric protein complex comprised of oligomers of a chimeric polypeptide subunit, said chimeric polypeptide subunit comprising
    (a) an influenza antigen derived from a naturally occurring oligomoric protein complex, and
    (b) a heterologous oligomerization domain,
    wherein the oligomerization domain mediates formation of an oligomeric chimeric protein complex from chimeric polypeptide subunits with the same degree of oligomerization as the naturally occurring oligomeric protein complex, said oligomeric chimeric protein complex eliciting a higher immune response than a subunit.

2. The chimeric protein according to claim 1 whereby said antigen is influenza neuraminidase or a functional fragment thereof.

3. The chimeric protein according to either of claims 1 or 2 whereby said oligomerization domain is a leucine zipper.

4. The recombinant oligomeric protein complex according to claim 1 whereby said recombinant oligomeric protein complex has a comparable enzymatic activity as the naturally occurring oligomeric protein complex.

5. The recombinant oligomeric protein complex according to claim 4 whereby said recombinant oligomeric protein complex is a tetramer.

6. The recombinant oligomeric protein complex according to claim 4 whereby said recombinant oligomeric protein complex is a dimer or a trimer.

7. The recombinant oligomeric protein complex according to claim 1 whereby said recombinant oligomeric protein complex elicits an antibody response similar to the antibody response elicited by the naturally occurring oligomeric protein complex.

8. A nucleic acid encoding the chimeric protein according to claim 1.

9. A nucleic acid comprising the sequence presented in SEQ ID NO:1.

10. An expression vector, comprising the nucleic acid according to claim 8 or claim 9.

11. An isolated host cell, comprising the expression vector according to claim 10.

* * * * *

SEQUENCE LISTING

```
<160> NUMBER OF SEQ ID NOS: 22

<210> SEQ ID NO 1
<211> LENGTH: 1350
<212> TYPE: DNA
<213> ORGANISM: Artificial Sequence
<220> FEATURE:
<223> OTHER INFORMATION: part of pACGCN4Nas
<220> FEATURE:
<221> NAME/KEY: CDS
<222> LOCATION: (1)..(1350)
<223> OTHER INFORMATION:

<400> SEQUENCE: 1 atg aag act atc att gct ttg agc tac att ttc tgt ctg gtt ttc gcc      48
Met Lys Thr Ile Ile Ala Leu Ser Tyr Ile Phe Cys Leu Val Phe Ala
1               5                   10                  15 caa gac ctt ggc ggt atg aaa caa atc gaa gac aag ctg gaa gaa atc      96
Gln Asp Leu Gly Gly Met Lys Gln Ile Glu Asp Lys Leu Glu Glu Ile
            20                  25                  30 ctt tcg aaa ctg tac cac atc gaa aac gag ctg gcc agg atc aag aaa     144
Leu Ser Lys Leu Tyr His Ile Glu Asn Glu Leu Ala Arg Ile Lys Lys
        35                  40                  45 ctg ctg ggc gaa ggt ggc aaa gag ata tgc ccc aaa tta gtg gaa tac     192
Leu Leu Gly Glu Gly Gly Lys Glu Ile Cys Pro Lys Leu Val Glu Tyr
    50                  55                  60
```

```
agg aat tgg tca aag cca caa tgt aaa att aca gga ttt gca cct ttc        240
Arg Asn Trp Ser Lys Pro Gln Cys Lys Ile Thr Gly Phe Ala Pro Phe
 65              70                  75                  80 tct aag gac aat tca att cgg ctt tct gct ggt ggg gac att tgg gtg        288
Ser Lys Asp Asn Ser Ile Arg Leu Ser Ala Gly Gly Asp Ile Trp Val
             85                  90                  95 acg aga gaa cct tat gtg tca tgc gat cct ggc aaa tgt tat caa ttt        336
Thr Arg Glu Pro Tyr Val Ser Cys Asp Pro Gly Lys Cys Tyr Gln Phe
                100                 105                 110 gca ctc ggg cag ggg acc aca cta gaa aac aaa cat tca aat gac aca        384
Ala Leu Gly Gln Gly Thr Thr Leu Glu Asn Lys His Ser Asn Asp Thr
            115                 120                 125 ata cat gat aga acc cct cat cga acc cta ttg atg aat gag ttg ggt        432
Ile His Asp Arg Thr Pro His Arg Thr Leu Leu Met Asn Glu Leu Gly
130                 135                 140 gtt cca ttt cac ttg gga acc agg caa gtg tgt ata gca tgg tcc agc        480
Val Pro Phe His Leu Gly Thr Arg Gln Val Cys Ile Ala Trp Ser Ser
145                 150                 155                 160 tca agt tgt cac gat gga aaa gca tgg ctg cat gtt tgt gtc act ggg        528
Ser Ser Cys His Asp Gly Lys Ala Trp Leu His Val Cys Val Thr Gly
                165                 170                 175 tat gat aaa aat gca act gct agc ttc att tac gat ggg agg ctt gta        576
Tyr Asp Lys Asn Ala Thr Ala Ser Phe Ile Tyr Asp Gly Arg Leu Val
            180                 185                 190 gac agc att ggt tca tgg tct caa aat atc ctc agg acc cag gag tcg        624
Asp Ser Ile Gly Ser Trp Ser Gln Asn Ile Leu Arg Thr Gln Glu Ser
        195                 200                 205 gaa tgt gtt tgt atc aat ggg act tgt aca gta gta atg act gat gga        672
Glu Cys Val Cys Ile Asn Gly Thr Cys Thr Val Val Met Thr Asp Gly
210                 215                 220 agt gct tca gga aga gct gat act aaa ata cta ttc att gaa gag ggg        720
Ser Ala Ser Gly Arg Ala Asp Thr Lys Ile Leu Phe Ile Glu Glu Gly
225                 230                 235                 240 aaa att gtt cat att agc cca ttg tca gga agt gct cag cat gta gag        768
Lys Ile Val His Ile Ser Pro Leu Ser Gly Ser Ala Gln His Val Glu
                245                 250                 255 gag tgt tcc tgt tat cct cga tat cct ggt gtc aga tgt atc tgc aga        816
Glu Cys Ser Cys Tyr Pro Arg Tyr Pro Gly Val Arg Cys Ile Cys Arg
            260                 265                 270 gac aac tgg aaa ggc tct aat agg cca gtc gta gat ata aat gtg aaa        864
Asp Asn Trp Lys Gly Ser Asn Arg Pro Val Val Asp Ile Asn Val Lys
        275                 280                 285 gat tat agc att gat tcc agt tat gtg tgc tca ggg ctt gtt ggc gac        912
Asp Tyr Ser Ile Asp Ser Ser Tyr Val Cys Ser Gly Leu Val Gly Asp
    290                 295                 300 aca ccc aga aaa aac gac aga tct agc agt agc tat tgc cgg aat cct        960
Thr Pro Arg Lys Asn Asp Arg Ser Ser Ser Ser Tyr Cys Arg Asn Pro
305                 310                 315                 320 aac aat gaa aaa ggg aat cac gga gtg aaa ggc tgg gcc ttt gac gat       1008
Asn Asn Glu Lys Gly Asn His Gly Val Lys Gly Trp Ala Phe Asp Asp
                325                 330                 335 gga aat gac gtg tgg atg gga aga acg atc agc gag gat tca cgc tca       1056
Gly Asn Asp Val Trp Met Gly Arg Thr Ile Ser Glu Asp Ser Arg Ser
            340                 345                 350 ggt tat gaa acc ttc aaa gtc att ggt ggt tgg tcc aca cct aat tcc       1104
Gly Tyr Glu Thr Phe Lys Val Ile Gly Gly Trp Ser Thr Pro Asn Ser
        355                 360                 365 aaa ttg cag ata aat agg caa gtc ata gtt gac agc gct aat agg tca       1152
Lys Leu Gln Ile Asn Arg Gln Val Ile Val Asp Ser Ala Asn Arg Ser
```

|  |  |  |  |  |  |  |  |  |  |  |  |  |  |  |  |
|---|---|---|---|---|---|---|---|---|---|---|---|---|---|---|---|
| | | | | 370 | | | | | 375 | | | | | 380 | |

```
ggt tat tct ggt att ttc tct gtt gag ggc aaa agc tgc atc aat agg      1200
Gly Tyr Ser Gly Ile Phe Ser Val Glu Gly Lys Ser Cys Ile Asn Arg
385                 390                 395                 400 tgc ttt tat gtg gag ttg ata agg gga agg gaa cag gaa act aga gta      1248
Cys Phe Tyr Val Glu Leu Ile Arg Gly Arg Glu Gln Glu Thr Arg Val
            405                 410                 415 tgg tgg acc tca aac agt att gtt gtg ttt tgt ggc act tca ggt acc      1296
Trp Trp Thr Ser Asn Ser Ile Val Val Phe Cys Gly Thr Ser Gly Thr
                420                 425                 430 tat ggg aca ggc tca tgg cct gat ggg gcg gac atc aat ctc atg cct      1344
Tyr Gly Thr Gly Ser Trp Pro Asp Gly Ala Asp Ile Asn Leu Met Pro
        435                 440                 445 ata taa                                                              1350
Ile
```

<210> SEQ ID NO 2
<211> LENGTH: 449
<212> TYPE: PRT
<213> ORGANISM: Artificial Sequence
<220> FEATURE:
<223> OTHER INFORMATION: part of pACGCN4Nas

<400> SEQUENCE: 2

```
Met Lys Thr Ile Ile Ala Leu Ser Tyr Ile Phe Cys Leu Val Phe Ala
1               5                   10                  15

Gln Asp Leu Gly Gly Met Lys Gln Ile Glu Asp Lys Leu Glu Glu Ile
            20                  25                  30

Leu Ser Lys Leu Tyr His Ile Glu Asn Glu Leu Ala Arg Ile Lys Lys
        35                  40                  45

Leu Leu Gly Glu Gly Gly Lys Glu Ile Cys Pro Lys Leu Val Glu Tyr
    50                  55                  60

Arg Asn Trp Ser Lys Pro Gln Cys Lys Ile Thr Gly Phe Ala Pro Phe
65                  70                  75                  80

Ser Lys Asp Asn Ser Ile Arg Leu Ser Ala Gly Gly Asp Ile Trp Val
                85                  90                  95

Thr Arg Glu Pro Tyr Val Ser Cys Asp Pro Gly Lys Cys Tyr Gln Phe
            100                 105                 110

Ala Leu Gly Gln Gly Thr Thr Leu Glu Asn Lys His Ser Asn Asp Thr
        115                 120                 125

Ile His Asp Arg Thr Pro His Arg Thr Leu Leu Met Asn Glu Leu Gly
    130                 135                 140

Val Pro Phe His Leu Gly Thr Arg Gln Val Cys Ile Ala Trp Ser Ser
145                 150                 155                 160

Ser Ser Cys His Asp Gly Lys Ala Trp Leu His Val Cys Val Thr Gly
                165                 170                 175

Tyr Asp Lys Asn Ala Thr Ala Ser Phe Ile Tyr Asp Gly Arg Leu Val
            180                 185                 190

Asp Ser Ile Gly Ser Trp Ser Gln Asn Ile Leu Arg Thr Gln Glu Ser
        195                 200                 205

Glu Cys Val Cys Ile Asn Gly Thr Cys Thr Val Val Met Thr Asp Gly
    210                 215                 220

Ser Ala Ser Gly Arg Ala Asp Thr Lys Ile Leu Phe Ile Glu Glu Gly
225                 230                 235                 240

Lys Ile Val His Ile Ser Pro Leu Ser Gly Ser Ala Gln His Val Glu
                245                 250                 255
```

```
Glu Cys Ser Cys Tyr Pro Arg Tyr Pro Gly Val Arg Cys Ile Cys Arg
            260                 265                 270

Asp Asn Trp Lys Gly Ser Asn Arg Pro Val Val Asp Ile Asn Val Lys
            275                 280                 285

Asp Tyr Ser Ile Asp Ser Tyr Val Cys Ser Gly Leu Val Gly Asp
            290                 295                 300

Thr Pro Arg Lys Asn Asp Arg Ser Ser Ser Tyr Cys Arg Asn Pro
305                 310                 315                 320

Asn Asn Glu Lys Gly Asn His Gly Val Lys Gly Trp Ala Phe Asp Asp
            325                 330                 335

Gly Asn Asp Val Trp Met Gly Arg Thr Ile Ser Glu Asp Ser Arg Ser
            340                 345                 350

Gly Tyr Glu Thr Phe Lys Val Ile Gly Gly Trp Ser Thr Pro Asn Ser
            355                 360                 365

Lys Leu Gln Ile Asn Arg Gln Val Ile Val Asp Ser Ala Asn Arg Ser
    370                 375                 380

Gly Tyr Ser Gly Ile Phe Ser Val Glu Gly Lys Ser Cys Ile Asn Arg
385                 390                 395                 400

Cys Phe Tyr Val Glu Leu Ile Arg Gly Arg Glu Gln Glu Thr Arg Val
                405                 410                 415

Trp Trp Thr Ser Asn Ser Ile Val Val Phe Cys Gly Thr Ser Gly Thr
            420                 425                 430

Tyr Gly Thr Gly Ser Trp Pro Asp Gly Ala Asp Ile Asn Leu Met Pro
            435                 440                 445

Ile

<210> SEQ ID NO 3
<211> LENGTH: 282
<212> TYPE: DNA
<213> ORGANISM: Artificial Sequence
<220> FEATURE:
<223> OTHER INFORMATION: part of pACsM2eGCN4
<220> FEATURE:
<221> NAME/KEY: CDS
<222> LOCATION: (1)..(282)
<223> OTHER INFORMATION:

<400> SEQUENCE: 3 atg cta cta gta aat cag tca cac caa ggc ttc aat aag gaa cac aca      48
Met Leu Leu Val Asn Gln Ser His Gln Gly Phe Asn Lys Glu His Thr
1               5                   10                  15 agc aag atg gta agc gct att gtt tta tat gtg ctt ttg gcg gcg gcg      96
Ser Lys Met Val Ser Ala Ile Val Leu Tyr Val Leu Leu Ala Ala Ala
            20                  25                  30 gcg cat tct gcc ttt gcc tct ctg ctg acc gaa gtt gaa acc cct atc     144
Ala His Ser Ala Phe Ala Ser Leu Leu Thr Glu Val Glu Thr Pro Ile
        35                  40                  45 aga aac gaa tgg ggg tgc aga tgc aac gat tca tcc gga ggt atg aaa     192
Arg Asn Glu Trp Gly Cys Arg Cys Asn Asp Ser Ser Gly Gly Met Lys
    50                  55                  60 caa atc gaa gac aag ctg gaa gaa atc ctt tcg aaa ctg tac cac atc     240
Gln Ile Glu Asp Lys Leu Glu Glu Ile Leu Ser Lys Leu Tyr His Ile
65                  70                  75                  80 gaa aac gag ctg gcc agg atc aag aaa ctg ctg ggc gaa tag              282
Glu Asn Glu Leu Ala Arg Ile Lys Lys Leu Leu Gly Glu
                85                  90

<210> SEQ ID NO 4
<211> LENGTH: 93
```

<212> TYPE: PRT
<213> ORGANISM: Artificial Sequence
<220> FEATURE:
<223> OTHER INFORMATION: part of pACsM2eGCN4

<400> SEQUENCE: 4

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ser Leu Leu Thr Glu Val Glu Thr Pro Ile
        35                  40                  45

Arg Asn Glu Trp Gly Cys Arg Cys Asn Asp Ser Ser Gly Gly Met Lys
    50                  55                  60

Gln Ile Glu Asp Lys Leu Glu Glu Ile Leu Ser Lys Leu Tyr His Ile
65                  70                  75                  80

Glu Asn Glu Leu Ala Arg Ile Lys Lys Leu Leu Gly Glu
                85                  90
```

<210> SEQ ID NO 5
<211> LENGTH: 1230
<212> TYPE: DNA
<213> ORGANISM: Artificial Sequence
<220> FEATURE:
<223> OTHER INFORMATION: part of pACsM2eGCN4C3d
<220> FEATURE:
<221> NAME/KEY: CDS
<222> LOCATION: (1)..(1230)
<223> OTHER INFORMATION:

<400> SEQUENCE: 5

```
atg cta cta gta aat cag tca cac caa ggc ttc aat aag gaa cac aca    48
Met Leu Leu Val Asn Gln Ser His Gln Gly Phe Asn Lys Glu His Thr
1               5                   10                  15 agc aag atg gta agc gct att gtt tta tat gtg ctt ttg gcg gcg gcg    96
Ser Lys Met Val Ser Ala Ile Val Leu Tyr Val Leu Leu Ala Ala Ala
            20                  25                  30 gcg cat tct gcc ttt gcc tct ctg ctg acc gaa gtt gaa acc cct atc   144
Ala His Ser Ala Phe Ala Ser Leu Leu Thr Glu Val Glu Thr Pro Ile
        35                  40                  45 aga aac gaa tgg ggg tgc aga tgc aac gat tca tcc gga ggt atg aaa   192
Arg Asn Glu Trp Gly Cys Arg Cys Asn Asp Ser Ser Gly Gly Met Lys
    50                  55                  60 caa atc gaa gac aag ctg gaa gaa atc ctt tcg aaa ctg tac cac atc   240
Gln Ile Glu Asp Lys Leu Glu Glu Ile Leu Ser Lys Leu Tyr His Ile
65                  70                  75                  80 gaa aac gag ctg gcc agg atc aag aaa ctg ctg ggc gaa gga tca ggt   288
Glu Asn Glu Leu Ala Arg Ile Lys Lys Leu Leu Gly Glu Gly Ser Gly
                85                  90                  95 tca ccg gat ctc gga tct acc ccc gca ggc tct ggg gaa cag aac atg   336
Ser Pro Asp Leu Gly Ser Thr Pro Ala Gly Ser Gly Glu Gln Asn Met
            100                 105                 110 att ggc atg aca cca aca gtc att gcg gta cac tac ctg gac cag acc   384
Ile Gly Met Thr Pro Thr Val Ile Ala Val His Tyr Leu Asp Gln Thr
        115                 120                 125 gaa cag tgg gag aag ttc ggc ata gag aag agg caa gag gcc ctg gag   432
Glu Gln Trp Glu Lys Phe Gly Ile Glu Lys Arg Gln Glu Ala Leu Glu
    130                 135                 140 ctc atc aag aaa ggg tac acc cag cag ctg gcc ttc aaa cag ccc agc   480
Leu Ile Lys Lys Gly Tyr Thr Gln Gln Leu Ala Phe Lys Gln Pro Ser
145                 150                 155                 160
```

```
tct gcc tat gct gcc ttc aac aac cgg ccc ccc agc acc tgg ctg aca      528
Ser Ala Tyr Ala Ala Phe Asn Asn Arg Pro Pro Ser Thr Trp Leu Thr
            165                 170                 175 gcc tac gtg gtc aag gtc ttc tct cta gct gcc aac ctc atc gcc atc      576
Ala Tyr Val Val Lys Val Phe Ser Leu Ala Ala Asn Leu Ile Ala Ile
        180                 185                 190 gac tct cac gtc ctg tgt ggg gct gtt aaa tgg ttg att ctg gag aaa      624
Asp Ser His Val Leu Cys Gly Ala Val Lys Trp Leu Ile Leu Glu Lys
    195                 200                 205 cag aag ccg gat ggt gtc ttt cag gag gat ggg ccc gtg att cac caa      672
Gln Lys Pro Asp Gly Val Phe Gln Glu Asp Gly Pro Val Ile His Gln
210                 215                 220 gaa atg att ggt ggc ttc cgg aac gcc aag gag gca gat gtg tca ctc      720
Glu Met Ile Gly Gly Phe Arg Asn Ala Lys Glu Ala Asp Val Ser Leu
225                 230                 235                 240 aca gcc ttc gtc ctc atc gca ctg cag gaa gcc agg gac atc tgt gag      768
Thr Ala Phe Val Leu Ile Ala Leu Gln Glu Ala Arg Asp Ile Cys Glu
                245                 250                 255 ggg cag gtc aat agc ctt cct ggg agc atc aac aag gca ggg gag tat      816
Gly Gln Val Asn Ser Leu Pro Gly Ser Ile Asn Lys Ala Gly Glu Tyr
            260                 265                 270 att gaa gcc agt tac atg aac ctg cag aga cca tac aca gtg gcc att      864
Ile Glu Ala Ser Tyr Met Asn Leu Gln Arg Pro Tyr Thr Val Ala Ile
        275                 280                 285 gct ggg tat gcc ctg gcc ctg atg aac aaa ctg gag gaa cct tac ctc      912
Ala Gly Tyr Ala Leu Ala Leu Met Asn Lys Leu Glu Glu Pro Tyr Leu
    290                 295                 300 ggc aag ttt ctg aac aca gcc aaa gat cgg aac cgc tgg gag gag cct      960
Gly Lys Phe Leu Asn Thr Ala Lys Asp Arg Asn Arg Trp Glu Glu Pro
305                 310                 315                 320 gac cag cag ctc tac aac gta gag gcc aca tcc tac gcc ctc ctg gcc     1008
Asp Gln Gln Leu Tyr Asn Val Glu Ala Thr Ser Tyr Ala Leu Leu Ala
                325                 330                 335 ctg ctg ctg ctg aaa gac ttt gac tct gtg ccc cct gta gtg cgc tgg     1056
Leu Leu Leu Leu Lys Asp Phe Asp Ser Val Pro Pro Val Val Arg Trp
            340                 345                 350 ctc aat gag caa aga tac tac gga ggc ggc tat ggc tcc acc cag gct     1104
Leu Asn Glu Gln Arg Tyr Tyr Gly Gly Gly Tyr Gly Ser Thr Gln Ala
        355                 360                 365 acc ttc atg gta ttc caa gcc ttg gcc caa tat caa aca gat gtc cct     1152
Thr Phe Met Val Phe Gln Ala Leu Ala Gln Tyr Gln Thr Asp Val Pro
    370                 375                 380 gac cat aag gac ttg aac atg gat gtg tcc ttc cac ctc ccc agc agt     1200
Asp His Lys Asp Leu Asn Met Asp Val Ser Phe His Leu Pro Ser Ser
385                 390                 395                 400 gga tct gaa gag ttc gga tcg gat cct tga                             1230
Gly Ser Glu Glu Phe Gly Ser Asp Pro
                405
```

<210> SEQ ID NO 6
<211> LENGTH: 409
<212> TYPE: PRT
<213> ORGANISM: Artificial Sequence
<220> FEATURE:
<223> OTHER INFORMATION: part of pACsM2eGCN4C3d

<400> SEQUENCE: 6

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30
```

```
Ala His Ser Ala Phe Ala Ser Leu Leu Thr Glu Val Glu Thr Pro Ile
            35                  40                  45

Arg Asn Glu Trp Gly Cys Arg Cys Asn Asp Ser Ser Gly Gly Met Lys
 50                  55                  60

Gln Ile Glu Asp Lys Leu Glu Ile Leu Ser Lys Leu Tyr His Ile
 65                  70                  75                  80

Glu Asn Glu Leu Ala Arg Ile Lys Lys Leu Leu Gly Gly Gly Ser Gly
                85                  90                  95

Ser Pro Asp Leu Gly Ser Thr Pro Ala Gly Ser Gly Glu Gln Asn Met
            100                 105                 110

Ile Gly Met Thr Pro Thr Val Ile Ala Val His Tyr Leu Asp Gln Thr
            115                 120                 125

Glu Gln Trp Glu Lys Phe Gly Ile Glu Lys Arg Gln Glu Ala Leu Glu
            130                 135                 140

Leu Ile Lys Lys Gly Tyr Thr Gln Gln Leu Ala Phe Lys Gln Pro Ser
145                 150                 155                 160

Ser Ala Tyr Ala Ala Phe Asn Asn Arg Pro Pro Ser Thr Trp Leu Thr
                165                 170                 175

Ala Tyr Val Val Lys Val Phe Ser Leu Ala Ala Asn Leu Ile Ala Ile
                180                 185                 190

Asp Ser His Val Leu Cys Gly Ala Val Lys Trp Leu Ile Leu Glu Lys
            195                 200                 205

Gln Lys Pro Asp Gly Val Phe Gln Glu Asp Gly Pro Val Ile His Gln
            210                 215                 220

Glu Met Ile Gly Gly Phe Arg Asn Ala Lys Glu Ala Asp Val Ser Leu
225                 230                 235                 240

Thr Ala Phe Val Leu Ile Ala Leu Gln Glu Ala Arg Asp Ile Cys Glu
                245                 250                 255

Gly Gln Val Asn Ser Leu Pro Gly Ser Ile Asn Lys Ala Gly Glu Tyr
            260                 265                 270

Ile Glu Ala Ser Tyr Met Asn Leu Gln Arg Pro Tyr Thr Val Ala Ile
            275                 280                 285

Ala Gly Tyr Ala Leu Ala Leu Met Asn Lys Leu Glu Glu Pro Tyr Leu
            290                 295                 300

Gly Lys Phe Leu Asn Thr Ala Lys Asp Arg Asn Arg Trp Glu Glu Pro
305                 310                 315                 320

Asp Gln Gln Leu Tyr Asn Val Glu Ala Thr Ser Tyr Ala Leu Leu Ala
                325                 330                 335

Leu Leu Leu Leu Lys Asp Phe Asp Ser Val Pro Pro Val Val Arg Trp
            340                 345                 350

Leu Asn Glu Gln Arg Tyr Tyr Gly Gly Gly Tyr Gly Ser Thr Gln Ala
            355                 360                 365

Thr Phe Met Val Phe Gln Ala Leu Ala Gln Tyr Gln Thr Asp Val Pro
            370                 375                 380

Asp His Lys Asp Leu Asn Met Asp Val Ser Phe His Leu Pro Ser Ser
385                 390                 395                 400

Gly Ser Glu Glu Phe Gly Ser Asp Pro
                405

<210> SEQ ID NO 7
<211> LENGTH: 24
<212> TYPE: DNA
<213> ORGANISM: Artificial Sequence
<220> FEATURE:
```

<223> OTHER INFORMATION: primer BACfor

<400> SEQUENCE: 7
tttactgttt tcgtaacagt tttg                                               24

<210> SEQ ID NO 8
<211> LENGTH: 54
<212> TYPE: DNA
<213> ORGANISM: Artificial Sequence
<220> FEATURE:
<223> OTHER INFORMATION: primer GCN4nh

<400> SEQUENCE: 8
tacagaagct tgtcttcgat tgtttcata ccgccaaggt cttgggcgaa aacc              54

<210> SEQ ID NO 9
<211> LENGTH: 54
<212> TYPE: DNA
<213> ORGANISM: Artificial Sequence
<220> FEATURE:
<223> OTHER INFORMATION: primer GCN4cooh

<400> SEQUENCE: 9
atctgatcaa gaaactgctg ggcgaaggtg gcaaagagat atgccccaaa ttag              54

<210> SEQ ID NO 10
<211> LENGTH: 23
<212> TYPE: DNA
<213> ORGANISM: Artificial Sequence
<220> FEATURE:
<223> OTHER INFORMATION: primer BACrev

<400> SEQUENCE: 10
cattttatgt ttcaggttca ggg                                                23

<210> SEQ ID NO 11
<211> LENGTH: 25
<212> TYPE: DNA
<213> ORGANISM: Artificial Sequence
<220> FEATURE:
<223> OTHER INFORMATION: primer GP67s

<400> SEQUENCE: 11
gctactagta aatcagtcac accaa                                              25

<210> SEQ ID NO 12
<211> LENGTH: 33
<212> TYPE: DNA
<213> ORGANISM: Artificial Sequence
<220> FEATURE:
<223> OTHER INFORMATION: primer GP67a

<400> SEQUENCE: 12
cgaagcttgc cggcaaaggc agaatgcgcc gcc                                     33

<210> SEQ ID NO 13
<211> LENGTH: 30
<212> TYPE: DNA
<213> ORGANISM: Artificial Sequence
<220> FEATURE:
<223> OTHER INFORMATION: primer M2rev

<400> SEQUENCE: 13
accattccgg atgaatcgtt gcatctgcac                                         30

<210> SEQ ID NO 14
<211> LENGTH: 23
<212> TYPE: DNA
<213> ORGANISM: Artificial Sequence
<220> FEATURE:
<223> OTHER INFORMATION: primer M2Ss

<400> SEQUENCE: 14
tctctgctga ccgaagttga aac                                           23

<210> SEQ ID NO 15
<211> LENGTH: 50
<212> TYPE: DNA
<213> ORGANISM: Artificial Sequence
<220> FEATURE:
<223> OTHER INFORMATION: primer UM2ECa

<400> SEQUENCE: 15
cgaagcttac tagttcacgg atccccactt gaatcgttgc atctgcaccc              50

<210> SEQ ID NO 16
<211> LENGTH: 32
<212> TYPE: DNA
<213> ORGANISM: Artificial Sequence
<220> FEATURE:
<223> OTHER INFORMATION: primer GCN4for

<400> SEQUENCE: 16
agatttccgg aggtatgaaa caaatcgaag ac                                 32

<210> SEQ ID NO 17
<211> LENGTH: 31
<212> TYPE: DNA
<213> ORGANISM: Artificial Sequence
<220> FEATURE:
<223> OTHER INFORMATION: primer GCN4rev

<400> SEQUENCE: 17
ataggagatc tattcgccca gcagtttctt g                                  31

<210> SEQ ID NO 18
<211> LENGTH: 43
<212> TYPE: DNA
<213> ORGANISM: Artificial Sequence
<220> FEATURE:
<223> OTHER INFORMATION: primer GCNrev2

<400> SEQUENCE: 18
tattggatcc ggtgaacctg atccttcgcc cagcagtttc ttg                     43

<210> SEQ ID NO 19
<211> LENGTH: 52
<212> TYPE: DNA
<213> ORGANISM: Artificial Sequence
<220> FEATURE:
<223> OTHER INFORMATION: primer GCN4pos

<400> SEQUENCE: 19
agctggaaga aatcctttcg aaactgtacc acatcgaaaa cgagctggcc ag           52

<210> SEQ ID NO 20
<211> LENGTH: 52
<212> TYPE: DNA
<213> ORGANISM: Artificial Sequence
<220> FEATURE:
<223> OTHER INFORMATION: primer GCN4neg

```
-continued

<400> SEQUENCE: 20
gatcctggcc agctcgtttt cgatgtggta cagtttcgaa aggatttctt cc          52

<210> SEQ ID NO 21
<211> LENGTH: 35
<212> TYPE: DNA
<213> ORGANISM: Artificial Sequence
<220> FEATURE:
<223> OTHER INFORMATION: primer C3ds

<400> SEQUENCE: 21
ccgcgcccac ccgacgagat ctcggatcta ccccc                             35

<210> SEQ ID NO 22
<211> LENGTH: 38
<212> TYPE: DNA
<213> ORGANISM: Artificial Sequence
<220> FEATURE:
<223> OTHER INFORMATION: primer C3da

<400> SEQUENCE: 22
gcactagttc aaggatccga tccgaactct tcagatcc                          38
```